United States Patent
Fenton

(10) Patent No.: US 10,945,873 B2
(45) Date of Patent: *Mar. 16, 2021

(54) MULTI-PETALED MOUNTING MEMBERS FOR OSTOMY POUCHES

(71) Applicant: Marlen Manufacturing and Development Co., Bedford, OH (US)

(72) Inventor: Gary H. Fenton, Pepper Pike, OH (US)

(73) Assignee: MARLEN MANUFACTURING AND DEVELOPMENT CO., Bedford, OH (US)

( * ) Notice: Subject to any disclaimer, the term of this patent is extended or adjusted under 35 U.S.C. 154(b) by 671 days.

This patent is subject to a terminal disclaimer.

(21) Appl. No.: 15/548,282

(22) PCT Filed: Dec. 9, 2016

(86) PCT No.: PCT/US2016/065774
§ 371 (c)(1),
(2) Date: Aug. 2, 2017

(87) PCT Pub. No.: WO2017/075634
PCT Pub. Date: May 4, 2017

(65) Prior Publication Data
US 2018/0021165 A1    Jan. 25, 2018

Related U.S. Application Data

(60) Provisional application No. 62/335,110, filed on May 12, 2016.

(51) Int. Cl.
| A61F 5/445 | (2006.01) |
| A61F 5/448 | (2006.01) |
| A61F 5/443 | (2006.01) |

(52) U.S. Cl.
CPC .............. *A61F 5/445* (2013.01); *A61F 5/443* (2013.01); *A61F 2005/4483* (2013.01)

(58) Field of Classification Search
CPC combination set(s) only.
See application file for complete search history.

(56) References Cited

U.S. PATENT DOCUMENTS

D201,737 S    7/1965    Ilg
3,690,320 A    9/1972    Riely et al.
(Continued)

FOREIGN PATENT DOCUMENTS

EP    0272816 A2    6/1988
EP    0882437 A2    12/1998
(Continued)

OTHER PUBLICATIONS

International Search Report and Written Opinion issued in corresponding PCT application No. PCT/US2016/065774 dated Feb. 17, 2017, 10 pages.
(Continued)

*Primary Examiner* — Guy K Townsend
(74) *Attorney, Agent, or Firm* — Pearne & Gordon LLP

(57) ABSTRACT

A multi-petaled mounting member for an ostomy pouch is disclosed. The mounting member comprises a flexible plastic member comprising a central body portion, a surrounding rim, and an outer perimeter, a first double-sided adhesive substrate member comprising a first face, an opposite second face, and an outer perimeter, a second double-sided adhesive substrate member comprising a first face, an opposite second face, and a multi-petaled outer perimeter, and an adhesive skin barrier member comprising a first face, an opposite second face, and a multi-petaled outer perimeter. The perimeters of the first member and the adhesive skin barrier member substantially correspond in size and shape to the
(Continued)

perimeters of the flexible plastic member and the second member, respectively. The perimeter of the second member has a size greater than the perimeter of the flexible plastic member and a shape corresponding to 2 to 8 petals extending radially from the second member.

20 Claims, 7 Drawing Sheets

(56) References Cited

U.S. PATENT DOCUMENTS

| | | | |
|---|---|---|---|
| D257,063 S | 9/1980 | Galindo | |
| 4,592,750 A | 6/1986 | Kay | |
| 4,762,738 A | 8/1988 | Keyes et al. | |
| D303,574 S | 9/1989 | Steer | |
| D303,575 S | 9/1989 | Steer | |
| 4,988,343 A | 1/1991 | Ballan | |
| 5,207,652 A * | 5/1993 | Kay | A61M 25/02 128/DIG. 26 |
| D354,560 S | 1/1995 | Chase | |
| D379,654 S | 6/1997 | Holtermann | |
| D398,990 S | 9/1998 | Briggs et al. | |
| D398,991 S | 9/1998 | Briggs et al. | |
| D460,550 S | 7/2002 | Falconer | |
| 6,508,794 B1 | 1/2003 | Palumbo et al. | |
| 6,589,221 B1 | 7/2003 | Olsen et al. | |
| D487,313 S | 3/2004 | Mazzella | |
| D496,727 S | 9/2004 | Kubalak | |
| 6,790,200 B2 * | 9/2004 | Fenton | A61F 5/445 604/332 |
| 6,802,831 B2 | 10/2004 | Plass et al. | |
| 6,916,312 B2 | 7/2005 | Kondo et al. | |
| 7,049,478 B1 * | 5/2006 | Smith | A61F 13/067 128/892 |
| 7,101,357 B2 | 9/2006 | Tanaka et al. | |
| D533,273 S | 12/2006 | Witt | |
| 7,223,260 B2 | 5/2007 | Hansen et al. | |
| D552,237 S | 10/2007 | Needham et al. | |
| 7,586,019 B2 * | 9/2009 | Oelund | A61F 5/443 128/888 |
| D607,559 S | 1/2010 | Schena | |
| D618,791 S | 6/2010 | Schena | |
| 8,328,779 B2 | 12/2012 | Fenton | |
| 8,399,732 B2 | 3/2013 | Oelund et al. | |
| 8,409,157 B2 * | 4/2013 | Haggstrom | A61F 13/0209 604/315 |
| 8,409,158 B2 * | 4/2013 | Edvardsen | A61F 5/443 604/318 |
| D683,451 S | 5/2013 | Todd et al. | |
| D691,730 S | 10/2013 | Smith et al. | |
| 8,672,908 B2 | 3/2014 | Todd et al. | |
| D737,453 S | 8/2015 | Gergely et al. | |
| D744,090 S | 11/2015 | Bendix et al. | |
| D753,820 S | 4/2016 | Lohse | |
| D766,448 S | 9/2016 | Gergely et al. | |
| D768,294 S | 10/2016 | Brezoczky | |
| D778,435 S | 2/2017 | Grogan | |
| D785,189 S | 4/2017 | Dettmar | |
| 9,622,903 B2 * | 4/2017 | Israelson | A61F 5/443 604/318 |
| 10,470,918 B2 * | 11/2019 | Bendix | A61F 5/448 604/332 |
| 10,517,754 B2 * | 12/2019 | Praame | A61F 13/64 604/392 |
| 2002/0032418 A1 | 3/2002 | Iseke | |
| 2002/0032428 A1 * | 3/2002 | Lindstrom | A61F 13/64 604/392 |
| 2002/0088080 A1 | 7/2002 | Fenton | |
| 2003/0100920 A1 | 5/2003 | Akin et al. | |
| 2003/0236509 A1 | 12/2003 | Silvestrini | |
| 2004/0106908 A1 * | 6/2004 | Leise, Jr. | A61F 5/448 604/332 |
| 2006/0195053 A1 * | 8/2006 | Oelund | A61F 5/448 602/43 |
| 2006/0276763 A1 | 12/2006 | Keyes | |
| 2011/0218507 A1 * | 9/2011 | Andersen | A61F 5/445 604/338 |
| 2012/0143154 A1 * | 6/2012 | Edvardsen | A61F 5/4404 604/318 |
| 2012/0143155 A1 * | 6/2012 | Edvardsen | A61F 5/443 604/318 |
| 2014/0114265 A1 * | 4/2014 | Israelson | A61F 5/443 604/342 |
| 2017/0143535 A1 * | 5/2017 | Praame | A61F 5/4404 604/318 |
| 2017/0224523 A1 * | 8/2017 | Bendix | A61F 5/448 602/43 |
| 2018/0021164 A1 * | 1/2018 | Fenton | A61F 13/067 128/892 |
| 2018/0021165 A1 * | 1/2018 | Fenton | A61F 5/443 128/888 |
| 2018/0104089 A1 * | 4/2018 | Nyberg | A61F 13/0209 604/315 |
| 2018/0235801 A1 * | 8/2018 | Oellgaard | A61F 5/445 604/332 |
| 2019/0133812 A1 * | 5/2019 | Seres | A61F 5/445 604/338 |

FOREIGN PATENT DOCUMENTS

| | | | | |
|---|---|---|---|---|
| GB | 2311467 A | | 10/1997 | |
| JP | S63181758 A | | 7/1988 | |
| JP | H10248867 A | | 9/1998 | |
| JP | 1036292 | | 4/1999 | |
| JP | 1036293 | | 4/1999 | |
| JP | 2005514075 A | | 5/2005 | |
| JP | 2011521725 A | | 7/2011 | |
| WO | 2015180731 A1 | | 12/2015 | |
| WO | WO-2015180731 A1 * | | 12/2015 | A61F 5/443 |
| WO | 2016151303 A1 | | 9/2016 | |
| WO | 2017087993 A1 | | 5/2017 | |

OTHER PUBLICATIONS

"A New Vision in Patient Care Introducing Kwick-View from Marlen", Product Literature, Accessed: May 11, 2016, 1 Page, Marlen Manufacturing & Development Company, Bedford, Ohio, USA.

"MARLEN UltraLite One-Piece Disposable, Drainable System for Ileostomies and Colostomies", Product Literature, © 2006, 2 Pages, Marlen Mfg. & Dev. Co., Bedford, Ohio, USA.

"Marlen UltraMax One-Piece Disposable Ostomy System", Product Literature, © 2005, 3 Pages, Marlen Manufacturing & Development Company, Bedford, Ohio, USA.

"UltraMax Gemini 2-Piece Disposal Adhesive Ostomy System", Product Literature, © 2008, 3 Pages, Marlen Manufacturing & Development Company, Bedford, Ohio, USA.

"Ultra-Moldable, Ultra-Flexible UltraSeal Flexible Barrier Ring", Product Literature, © 2006, 1 Page, Marlen Manufacturing & Development Company, Bedford, Ohio, USA.

Applicant's Design U.S. Appl. No. 29/564,314, filed May 12, 2016; Inventor: Gary H. Fenton; Applicant and Assignee: Marlen Manufacturing and Development Co; Copies of Filing receipt, specification and drawings provided herewith.

Search Report for European Application No. 16861076.4 dated Dec. 12, 2019, 9 pages.

Notice of Reasons for Rejection for Japanese Patent Application No. 2018-559882 dated Dec. 3, 2019, 7 pages (English translation included).

Canadian Examination for Application No. 3,022,908 dated Sep. 23, 2019, 3 pages.

Search Report for European Application No. 16861076.4 dated Aug. 10, 2020, 7 pages.

* cited by examiner

A

B

A

B

A

B

A

B

MULTI-PETALED MOUNTING MEMBERS FOR OSTOMY POUCHES

FIELD OF THE INVENTION

The present invention relates generally to multi-petaled mounting members for ostomy pouches, and more particularly, to multi-petaled mounting members for ostomy pouches comprising (a) a flexible plastic member comprising a central body portion, a surrounding rim, and an outer perimeter, (b) a first double-sided adhesive substrate member comprising a first face, an opposite second face, and an outer perimeter, (c) a second double-sided adhesive substrate member comprising a first face, an opposite second face, and a multi-petaled outer perimeter, and (d) an adhesive skin barrier member comprising a first face, an opposite second face, and a multi-petaled outer perimeter, wherein (i) the outer perimeter of the first double-sided adhesive substrate member substantially corresponds in size and shape to the outer perimeter of the flexible plastic member, (ii) the multi-petaled outer perimeter of the second double-sided adhesive substrate member has a size greater than the outer perimeter of the flexible plastic member and a shape corresponding to 2 to 8 petals extending radially from the second double-sided adhesive substrate member, distributed uniformly around the second double-sided adhesive substrate member, and separated by notches that expand radially from the second double-sided adhesive substrate member, and (iii) the multi-petaled outer perimeter of the adhesive skin barrier member substantially corresponds in size and shape to the multi-petaled outer perimeter of the second double-sided adhesive substrate member.

BACKGROUND OF THE INVENTION

Ostomates are individuals that have undergone a surgery to create an opening in the body, termed an ostomy, that allows for discharge of body waste. The surgery includes preparation of a stoma, corresponding to the end of an organ such as the colon, small intestine, or ureter, that protrudes through the abdominal wall and through which the body waste is discharged. An ostomy appliance can be attached to a skin surface around the ostomy, termed a peristomal skin surface, for collection of the body waste.

Various types of ostomy appliances have been disclosed. For example, Fenton, U.S. Pat. No. 6,790,200, discloses an ostomy appliance and a mounting disc that include an ostomy pouch having a stoma receiving portal. The mounting disc is sealed about the portal and includes a flexible plastic disc having a convex central body portion and a surrounding annular rim. A first foam disc having an outer diameter corresponding to the outer diameter of the rim is adhesively adhered to the plastic disc. A second foam disc is adhered to an adhesive face of the first foam disc and has an outer diameter greater than the plastic disc. A hydrocolloid skin shield disc having an outer diameter corresponding to the outer diameter of the second foam disc is adhesively adhered to an adhesive face of the second disc.

Also for example, Fenton, U.S. Pat. No. 8,328,779, discloses a mounting assembly for an ostomy pouch. The assembly includes a body flange having an adhesive coating on one side adapted to be adhered to the peristomal skin surface of an ostomate. Diametrically opposed loops project from the edge of the flange and form pockets. An ostomy pouch having a stoma receiving opening surrounded by a stiffly flexible ring having diametrically opposed loops that cooperate with the pockets on the flange loops is also disclosed. An adhesive coating is provided on the flexible ring and flange. When the loops on the flexible ring are aligned with the pockets on the flange, the flange and ring may be adhesively interlocked to attach the pouch to the body flange.

Much effort has been invested in improving ostomy appliances, and in developing accessories, to make use of ostomy appliances as comfortable as possible. Yet ostomates still may have difficulty initially identifying an ostomy appliance that provides a suitable fit and still may be reluctant to try different ostomy appliances based on concern that a different fit will not be suitable.

Accordingly, a need exists for ostomy appliances that can provide improved fit and increased comfort for ostomates generally.

BRIEF SUMMARY OF THE INVENTION

A multi-petaled mounting member for an ostomy pouch is disclosed. The multi-petaled mounting member comprises (a) a flexible plastic member comprising a central body portion, a surrounding rim, and an outer perimeter, (b) a first double-sided adhesive substrate member comprising a first face, an opposite second face, and an outer perimeter, (c) a second double-sided adhesive substrate member comprising a first face, an opposite second face, and a multi-petaled outer perimeter, and (d) an adhesive skin barrier member comprising a first face, an opposite second face, and a multi-petaled outer perimeter. The outer perimeter of the first double-sided adhesive substrate member substantially corresponds in size and shape to the outer perimeter of the flexible plastic member. The second face of the first double-sided adhesive substrate member is adhered to the central body portion and the surrounding rim of the flexible plastic member. The multi-petaled outer perimeter of the second double-sided adhesive substrate member has a size greater than the outer perimeter of the flexible plastic member and a shape corresponding to 2 to 8 petals extending radially from the second double-sided adhesive substrate member, distributed uniformly around the second double-sided adhesive substrate member, and separated by notches that expand radially from the second double-sided adhesive substrate member. The second face of the second double-sided adhesive substrate member is adhered to the first face of the first double-sided adhesive substrate member. The multi-petaled outer perimeter of the adhesive skin barrier member substantially corresponds in size and shape to the multi-petaled outer perimeter of the second double-sided adhesive substrate member. The second face of the adhesive skin barrier member is adhered to the first face of the second double-sided adhesive substrate member.

In accordance with some examples, (i) the central body portion of the flexible plastic member has a first face and an opposite second face, (ii) the first face of the central body portion is convex, (iii) the second face of the central body portion is concave, and (iv) the second face of the first double-sided adhesive substrate member is adhered to the central body portion on the convex first face of the central body portion.

Also in accordance with some examples, (i) the central body portion of the flexible plastic member has a first face and an opposite second face, (ii) the first face of the central body portion is flat, (iii) the second face of the central body portion is flat, and (iv) the second face of the first double-sided adhesive substrate member is adhered to the central body portion on the flat first face of the central body portion.

Also in accordance with some examples, the 2 to 8 petals each have a width that first increases, then decreases, radially outwardly from the second double-sided adhesive substrate member.

Also in accordance with some examples, the second double-sided adhesive substrate member has a maximum radius, and at least 50% of the multi-petaled outer perimeter of the second double-sided adhesive substrate member extends to the maximum radius of the second double-sided adhesive substrate member.

Also in accordance with some examples, the shape of the multi-petaled outer perimeter of the second double-sided adhesive substrate member corresponds to 3 to 6 petals.

Also in accordance with some examples, the surrounding rim of the flexible plastic member is substantially annular.

Also in accordance with some examples, the flexible plastic member further comprises mounting loops that are diametrically opposed and that extend radially outwardly from the surrounding rim to no further than the multi-petaled outer perimeter of the second double-sided adhesive substrate member and the multi-petaled outer perimeter of the adhesive skin barrier member.

Also in accordance with some examples, the adhesive skin barrier member comprises an elastomer hydrocolloid mixture.

Also in accordance with some examples, the first double-sided adhesive substrate member comprises a foam layer.

Also in accordance with some examples, the second double-sided adhesive substrate member comprises a foam layer.

Also in accordance with some examples, the multi-petaled mounting member further comprises a removable protective film, wherein the removable protective film covers the first face of the adhesive skin barrier member.

Also in accordance with some examples, each of the flexible plastic member, the first double-sided adhesive substrate member, the second double-sided adhesive substrate member, and the adhesive skin barrier member have a stoma inlet portal, centrally positioned and extending therethrough.

An ostomy appliance also is disclosed. The ostomy appliance comprises a multi-petaled mounting member. The ostomy appliance also comprises an ostomy pouch.

The multi-petaled mounting member comprises (a) a flexible plastic member comprising a central body portion, a surrounding rim, and an outer perimeter, (b) a first double-sided adhesive substrate member comprising a first face, an opposite second face, and an outer perimeter, (c) a second double-sided adhesive substrate member comprising a first face, an opposite second face, and a multi-petaled outer perimeter, and (d) an adhesive skin barrier member comprising a first face, an opposite second face, and a multi-petaled outer perimeter. The outer perimeter of the first double-sided adhesive substrate member substantially corresponds in size and shape to the outer perimeter of the flexible plastic member. The second face of the first double-sided adhesive substrate member is adhered to the central body portion and the surrounding rim of the flexible plastic member. The multi-petaled outer perimeter of the second double-sided adhesive substrate member has a size greater than the outer perimeter of the flexible plastic member and a shape corresponding to 2 to 8 petals extending radially from the second double-sided adhesive substrate member, distributed uniformly around the second double-sided adhesive substrate member, and separated by notches that expand radially from the second double-sided adhesive substrate member. The second face of the second double-sided adhesive substrate member is adhered to the first face of the first double-sided adhesive substrate member. The multi-petaled outer perimeter of the adhesive skin barrier member substantially corresponds in size and shape to the multi-petaled outer perimeter of the second double-sided adhesive substrate member. The second face of the adhesive skin barrier member is adhered to the first face of the second double-sided adhesive substrate member.

The ostomy pouch comprises a proximal sheet of plastic film and a distal sheet of plastic film, the proximal sheet and the distal sheet being sealed at their respective peripheries to form the ostomy pouch. The proximal sheet comprises a stoma inlet portal having an inner perimeter and a zone surrounding the inner perimeter. The surrounding rim of the flexible plastic member further comprises an inner perimeter. The inner perimeter of the surrounding rim of the flexible plastic member substantially corresponds in size and shape to the inner perimeter of the stoma inlet portal of the proximal sheet. The surrounding rim of the flexible plastic member is sealed to the zone surrounding the inner perimeter of the proximal sheet.

In accordance with some examples, (i) the central body portion of the flexible plastic member has a first face and an opposite second face, (ii) the first face of the central body portion is convex, (iii) the second face of the central body portion is concave, and (iv) the second face of the first double-sided adhesive substrate member is adhered to the central body portion on the convex first face of the central body portion.

Also in accordance with some examples, (i) the central body portion of the flexible plastic member has a first face and an opposite second face, (ii) the first face of the central body portion is flat, (iii) the second face of the central body portion is flat, and (iv) the second face of the first double-sided adhesive substrate member is adhered to the central body portion on the flat first face of the central body portion.

Also in accordance with some examples, the 2 to 8 petals each have a width that first increases, then decreases, radially outwardly from the second double-sided adhesive substrate member.

Also in accordance with some examples, the second double-sided adhesive substrate member has a maximum radius, and at least 50% of the multi-petaled outer perimeter of the second double-sided adhesive substrate member extends to the maximum radius of the second double-sided adhesive substrate member.

Also in accordance with some examples, the shape of the multi-petaled outer perimeter of the second double-sided adhesive substrate member corresponds to 3 to 6 petals.

Also in accordance with some examples, the surrounding rim of the flexible plastic member is substantially annular.

Also in accordance with some examples, the flexible plastic member further comprises mounting loops that are diametrically opposed and that extend radially outwardly from the surrounding rim to no further than the multi-petaled outer perimeter of the second double-sided adhesive substrate member and the multi-petaled outer perimeter of the adhesive skin barrier member.

Also in accordance with some examples, the adhesive skin barrier member comprises an elastomer hydrocolloid mixture.

Also in accordance with some examples, the first double-sided adhesive substrate member comprises a foam layer.

Also in accordance with some examples, the second double-sided adhesive substrate member comprises a foam layer.

Also in accordance with some examples, the multi-petaled mounting member further comprises a removable protective film, wherein the removable protective film covers the first face of the adhesive skin barrier member.

Also in accordance with some examples, each of the flexible plastic member, the first double-sided adhesive substrate member, the second double-sided adhesive substrate member, and the adhesive skin barrier member have a stoma inlet portal, centrally positioned and extending therethrough.

Also disclosed is a method of adhering an ostomy appliance to an ostomate at a peristomal skin surface of the ostomate. In accordance with the method, the ostomy appliance comprises a multi-petaled mounting member. The ostomy appliance also comprises an ostomy pouch.

The multi-petaled mounting member comprises (a) a flexible plastic member comprising a central body portion, a surrounding rim, and an outer perimeter, (b) a first double-sided adhesive substrate member comprising a first face, an opposite second face, and an outer perimeter, (c) a second double-sided adhesive substrate member comprising a first face, an opposite second face, and a multi-petaled outer perimeter, and (d) an adhesive skin barrier member comprising a first face, an opposite second face, and a multi-petaled outer perimeter. The outer perimeter of the first double-sided adhesive substrate member substantially corresponds in size and shape to the outer perimeter of the flexible plastic member. The second face of the first double-sided adhesive substrate member is adhered to the central body portion and the surrounding rim of the flexible plastic member. The multi-petaled outer perimeter of the second double-sided adhesive substrate member has a size greater than the outer perimeter of the flexible plastic member and a shape corresponding to 2 to 8 petals extending radially from the second double-sided adhesive substrate member, distributed uniformly around the second double-sided adhesive substrate member, and separated by notches that expand radially from the second double-sided adhesive substrate member. The second face of the second double-sided adhesive substrate member is adhered to the first face of the first double-sided adhesive substrate member. The multi-petaled outer perimeter of the adhesive skin barrier member substantially corresponds in size and shape to the multi-petaled outer perimeter of the second double-sided adhesive substrate member. The second face of the adhesive skin barrier member is adhered to the first face of the second double-sided adhesive substrate member.

The multi-petaled mounting member further comprises a removable protective film, wherein the removable protective film covers the first face of the adhesive skin barrier member.

Each of the flexible plastic member, the first double-sided adhesive substrate member, the second double-sided adhesive substrate member, and the adhesive skin barrier member have a stoma inlet portal, centrally positioned and extending therethrough.

The ostomy pouch comprises a proximal sheet of plastic film and a distal sheet of plastic film, the proximal sheet and the distal sheet being sealed at their respective peripheries to form the ostomy pouch. The proximal sheet comprises a stoma inlet portal having an inner perimeter and a zone surrounding the inner perimeter. The surrounding rim of the flexible plastic member further comprises an inner perimeter. The inner perimeter of the surrounding rim of the flexible plastic member substantially corresponds in size and shape to the inner perimeter of the stoma inlet portal of the proximal sheet. The surrounding rim of the flexible plastic member is sealed to the zone surrounding the inner perimeter of the proximal sheet.

The method comprises a step of (1) removing the removable protective film from the first face of the adhesive skin barrier member. The method also comprises a step of (2) placing the first face of the adhesive skin barrier member at the peristomal region of the ostomate, such that the stoma inlet portal of the proximal sheet of the ostomy pouch and the stoma inlet portals of the flexible plastic member, the first double-sided adhesive substrate member, the second double-sided adhesive substrate member, and the adhesive skin barrier member are aligned with a stoma of the ostomate. In accordance with the method, the ostomy appliance is thereby adhered to the ostomate at the peristomal skin surface of the ostomate.

In accordance with some examples, the ostomy appliance adheres to the ostomate at the peristomal skin surface of the ostomate with a smooth fit.

Also in accordance with some examples, the ostomy appliance adheres to the ostomate at the peristomal skin surface of the ostomate without application of adhesive tape to the ostomy appliance or to the ostomate.

Also disclosed is another method of adhering an ostomy appliance to an ostomate at a peristomal skin surface of the ostomate. In accordance with the method, the ostomy appliance comprises a multi-petaled mounting member. The ostomy appliance also comprises an ostomy pouch.

The multi-petaled mounting member comprises (a) a flexible plastic member comprising a central body portion, a surrounding rim, and an outer perimeter, (b) a first double-sided adhesive substrate member comprising a first face, an opposite second face, and an outer perimeter, (c) a second double-sided adhesive substrate member comprising a first face, an opposite second face, and a multi-petaled outer perimeter, and (d) an adhesive skin barrier member comprising a first face, an opposite second face, and a multi-petaled outer perimeter. The outer perimeter of the first double-sided adhesive substrate member substantially corresponds in size and shape to the outer perimeter of the flexible plastic member. The second face of the first double-sided adhesive substrate member is adhered to the central body portion and the surrounding rim of the flexible plastic member. The multi-petaled outer perimeter of the second double-sided adhesive substrate member has a size greater than the outer perimeter of the flexible plastic member and a shape corresponding to 2 to 8 petals extending radially from the second double-sided adhesive substrate member, distributed uniformly around the second double-sided adhesive substrate member, and separated by notches that expand radially from the second double-sided adhesive substrate member. The second face of the second double-sided adhesive substrate member is adhered to the first face of the first double-sided adhesive substrate member. The multi-petaled outer perimeter of the adhesive skin barrier member substantially corresponds in size and shape to the multi-petaled outer perimeter of the second double-sided adhesive substrate member. The second face of the adhesive skin barrier member is adhered to the first face of the second double-sided adhesive substrate member.

The multi-petaled mounting member further comprises a removable protective film, wherein the removable protective film covers the first face of the adhesive skin barrier member.

The ostomy pouch comprises a proximal sheet of plastic film and a distal sheet of plastic film, the proximal sheet and the distal sheet being sealed at their respective peripheries to form the ostomy pouch. The proximal sheet comprises a stoma inlet portal having an inner perimeter and a zone surrounding the inner perimeter. The surrounding rim of the flexible plastic member further comprises an inner perimeter. The inner perimeter of the surrounding rim of the flexible plastic member substantially corresponds in size and shape to the inner perimeter of the stoma inlet portal of the proximal sheet. The surrounding rim of the flexible plastic member is sealed to the zone surrounding the inner perimeter of the proximal sheet.

The method comprises a step of (1) removing the removable protective film from the first face of the adhesive skin barrier member. The method also comprises a step of (2) cutting a stoma inlet portal through at least the adhesive skin barrier member, such that each of the flexible plastic member, the first double-sided adhesive substrate member, the second double-sided adhesive substrate member, and the adhesive skin barrier member have a stoma inlet portal, centrally positioned and extending therethrough. The method also comprises a step of (3) placing the first face of the adhesive skin barrier member at the peristomal region of the ostomate, such that the stoma inlet portal of the proximal sheet of the ostomy pouch and the stoma inlet portals of the flexible plastic member, the first double-sided adhesive substrate member, the second double-sided adhesive substrate member, and the adhesive skin barrier member are aligned with a stoma of the ostomate. In accordance with the method, the ostomy appliance is thereby adhered to the ostomate at the peristomal skin surface of the ostomate.

In some examples, the ostomy appliance adheres to the ostomate at the peristomal skin surface of the ostomate with a smooth fit.

Also in some examples, the ostomy appliance adheres to the ostomate at the peristomal skin surface of the ostomate without application of adhesive tape to the ostomy appliance or to the ostomate.

BRIEF DESCRIPTION OF THE DRAWINGS

These and other features, aspects, and advantages of the claimed multi-petaled mounting members, ostomy appliances, and methods are better understood when the following detailed description is read with reference to the accompanying drawings, in which:

DETAILED DESCRIPTION OF THE INVENTION

Figure 1:
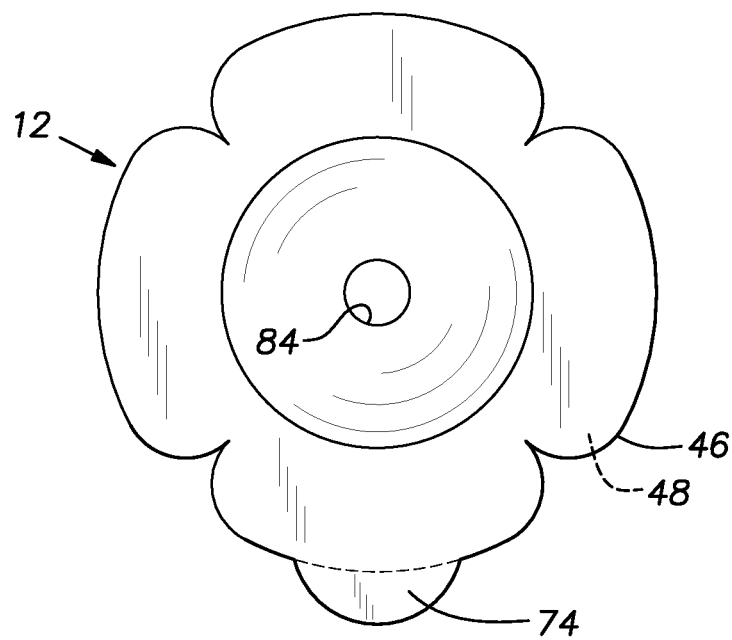
FIG. 1 is a perspective view of a multi-petaled mounting member for an ostomy pouch as disclosed.
Figure 3:
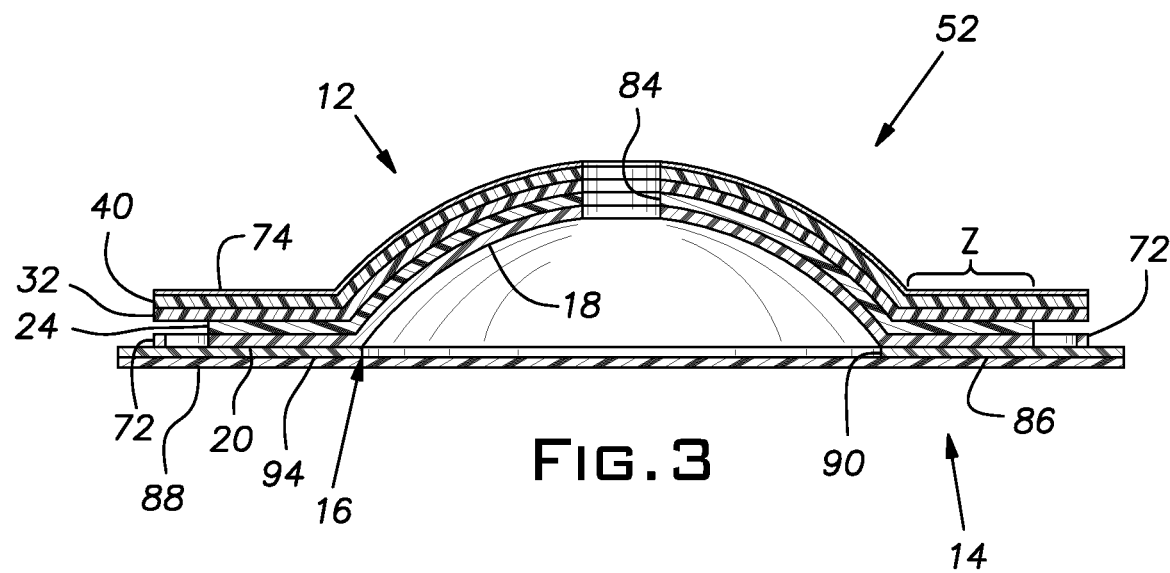
FIG. 3 is a sectional view, the plane of the section being indicated by the line 3-3 in FIG. 2.
Figure 2:
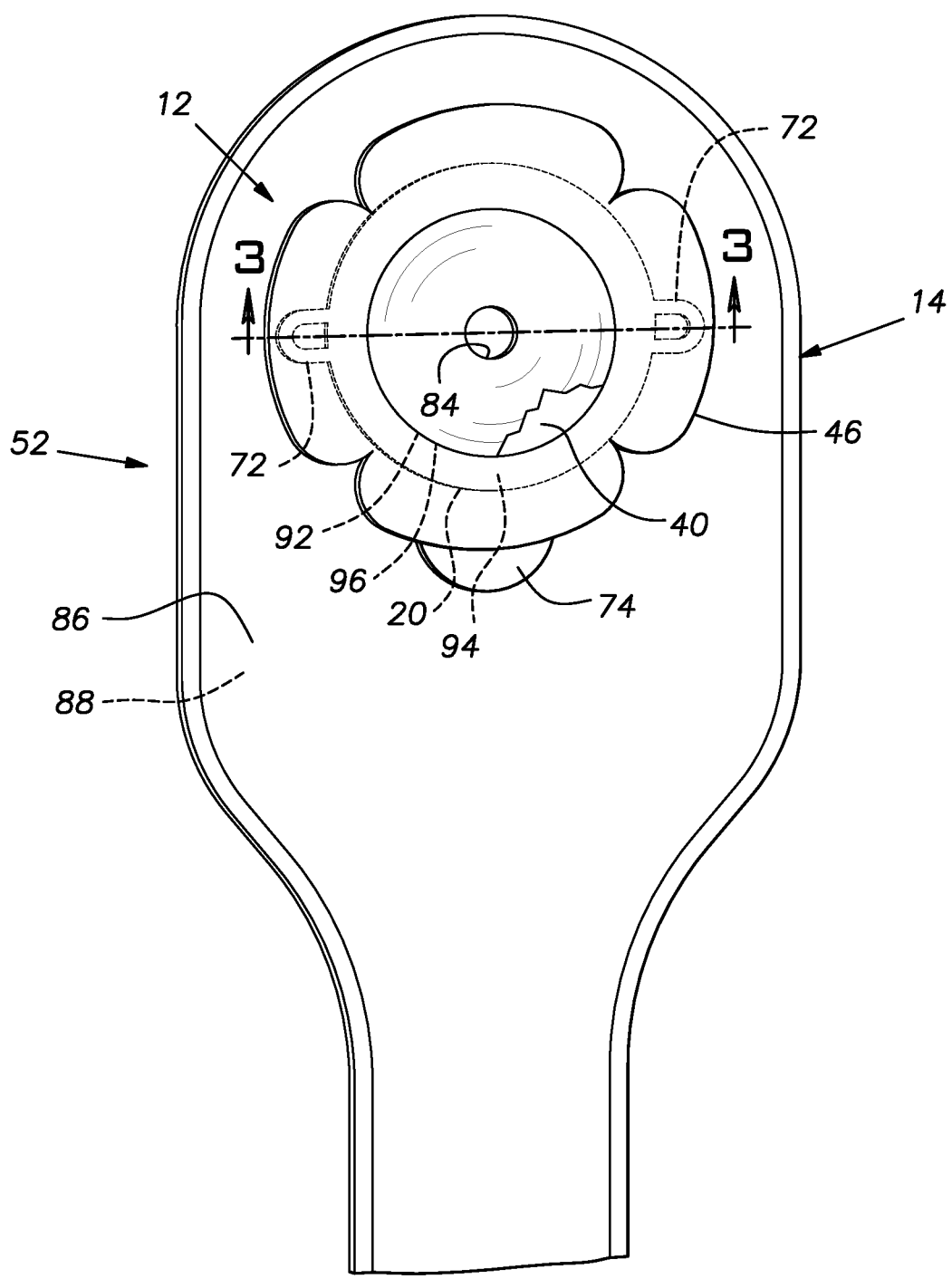
FIG. 2 is a perspective view of an ostomy appliance comprising a multi-petaled mounting member and an ostomy pouch, as disclosed.
Figure 4:
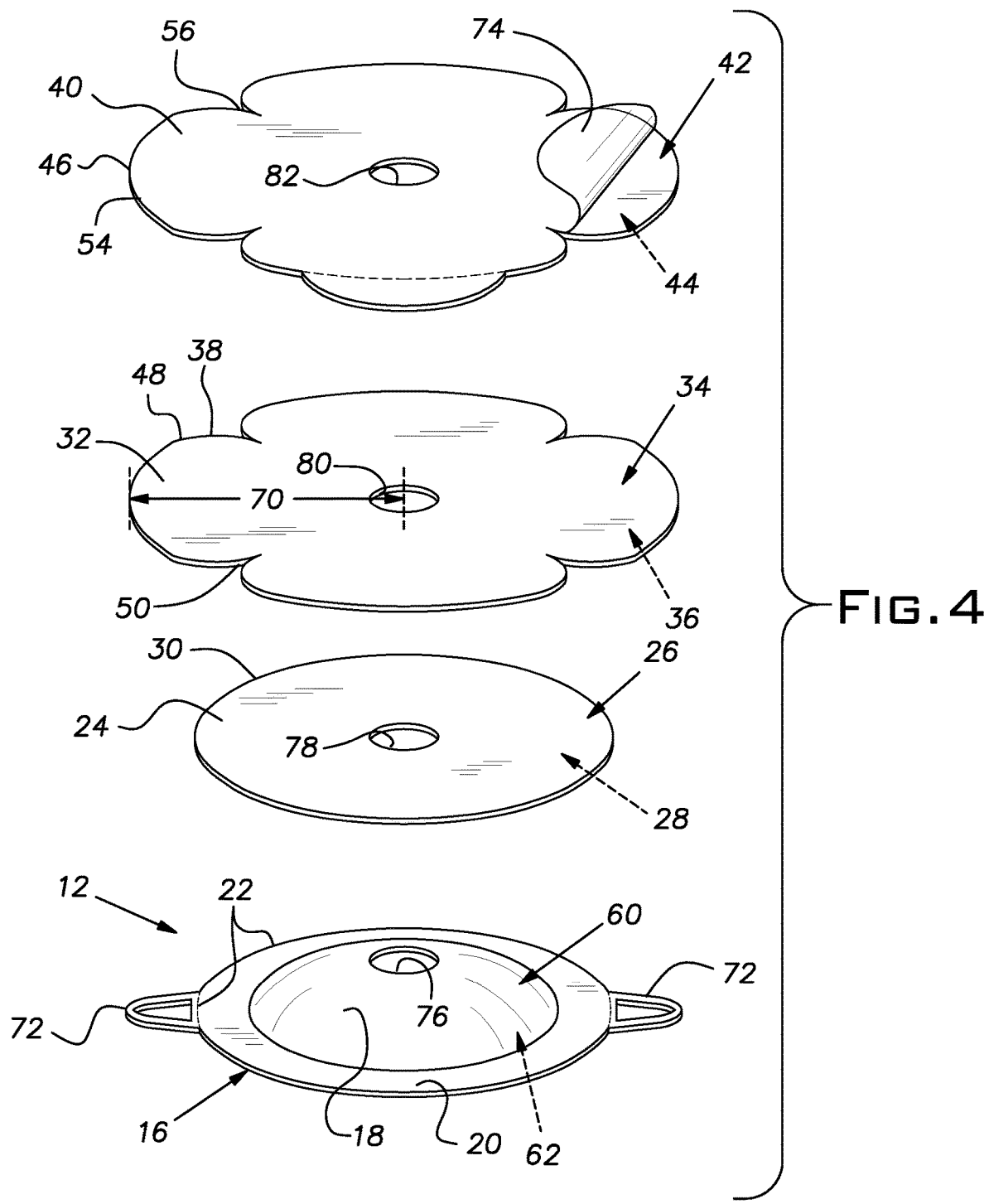
FIG. 4 is an exploded view of a multi-petaled mounting member for an ostomy pouch as disclosed, in which the multi-petaled mounting member is convex.

A multi-petaled mounting member 12 for an ostomy pouch 14 is disclosed (FIG. 1 and FIG. 2). The multi-petaled mounting member 12 comprises (a) a flexible plastic member 16 comprising a central body portion 18, a surrounding rim 20, and an outer perimeter 22, (b) a first double-sided adhesive substrate member 24 comprising a first face 26, an opposite second face 28, and an outer perimeter 30, (c) a second double-sided adhesive substrate member 32 comprising a first face 34, an opposite second face 36, and a multi-petaled outer perimeter 38, and (d) an adhesive skin barrier member 40 comprising a first face 42, an opposite second face 44, and a multi-petaled outer perimeter 46 (FIG. 3 and FIG. 4). The outer perimeter 30 of the first double-sided adhesive substrate member 24 substantially corresponds in size and shape to the outer perimeter 22 of the flexible plastic member 16. The second face 28 of the first double-sided adhesive substrate member 24 is adhered to the central body portion 18 and the surrounding rim 20 of the flexible plastic member 16. The multi-petaled outer perimeter 38 of the second double-sided adhesive substrate member 32 has a size greater than the outer perimeter 22 of the flexible plastic member 16 and a shape corresponding to 2 to 8 petals 48 extending radially from the second double-sided adhesive substrate member 32, distributed uniformly around the second double-sided adhesive substrate member 32, and separated by notches 50 that expand radially from the second double-sided adhesive substrate member 32. The second face 36 of the second double-sided adhesive substrate member 32 is adhered to the first face 26 of the first double-sided adhesive substrate member 24. The multi-petaled outer perimeter 46 of the adhesive skin barrier member 40 substantially corresponds in size and shape to the multi-petaled outer perimeter 38 of the second double-sided adhesive substrate member 32. The second face 44 of the adhesive skin barrier member 40 is adhered to the first face 34 of the second double-sided adhesive substrate member 32.

The multi-petaled mounting member 12 provides improved fit of the adhesive skin barrier member 40 at a peristomal region of an ostomate, e.g. such that a corresponding ostomy appliance 52 adheres to the ostomate at the peristomal skin surface of the ostomate with a smooth fit and/or that the ostomy appliance 52 adheres to the ostomate at the peristomal skin surface of the ostomate without need for application of adhesive tape to the ostomy appliance 52 or to the ostomate. In view of the size and shape of the multi-petaled outer perimeter 38 of the second double-sided adhesive substrate member 32, and given that the multi-petaled outer perimeter 46 of the adhesive skin barrier member 40 substantially corresponds in size and shape to the multi-petaled outer perimeter 38 of the second double-sided adhesive substrate member 32, the multi-petaled outer perimeter 46 of the adhesive skin barrier member 40 also has a shape corresponding to 2 to 8 petals 54 extending radially from the adhesive skin barrier member 40, distributed uniformly around the adhesive skin barrier member 40, and separated by notches 56 that expand radially from the adhesive skin barrier member 40. This configuration allows the multi-petaled mounting member 12 to be adapted to a peristomal skin surface of an ostomate, without undesirable bunching upon application, and this applies across a range of peristomal skin surface contours of ostomates, e.g. for ostomates with peristomal skin surfaces that are flat, curved, bulging, and/or irregular. As the pouch fills with body waste, the adhesive skin barrier member will remain secure and stay attached at the peristomal skin surface of the ostomate, and not peel away. Thus, this configuration provides improved fit and increased comfort for ostomates generally.

The flexible plastic member 16 can be made from, for example, a copolymer of ethylene and vinyl acetate, e.g. the ELVAX(R) 450 product of DuPont.

The first double-sided adhesive substrate member 24 can be made from, for example, a foam layer, a thermoplastic layer, a polypropylene layer, a polyethylene layer, a nonwoven layer, and/or a film layer. Also, the first double-sided adhesive substrate member 24 can be a soft, resilient double-sided adhesive substrate member. Thus, in some examples the first double-sided adhesive substrate member 24 can comprise a foam layer, e.g. a soft, resilient foam layer.

The second double-sided adhesive substrate member 32 also can be made from, for example, a foam layer, a thermoplastic layer, a polypropylene layer, a polyethylene layer, a nonwoven layer, and/or a film layer. Also, the second double-sided adhesive substrate member 32 can be a soft, resilient double-sided adhesive substrate member. Thus, in some examples the second double-sided adhesive substrate member 32 can comprise a foam layer, e.g. a soft, resilient foam layer.

The adhesive skin barrier member 40 can be made from a suitable material for providing a skin barrier, can be pliable, and can have both dry tack and wet tack.

As noted, the outer perimeter 30 of the first double-sided adhesive substrate member 24 substantially corresponds in size and shape to the outer perimeter 22 of the flexible plastic member 16. For example, the outer perimeter 30 of the first double-sided adhesive substrate member 24 can correspond in size and shape to the outer perimeter 22 of the flexible plastic member 16 such that when the first double-sided adhesive substrate member 24 is positioned on the flexible plastic member 16 in an orientation maximizing alignment thereof, the outer perimeter 30 of the first double-sided adhesive substrate member 24 extends not more than, for example, 10 mm, 3 mm, or 1 mm beyond the outer perimeter 22 of the flexible plastic member 16 at any point along the outer perimeter 30 of the first double-sided adhesive substrate member 24. Also for example, the outer perimeter 30 of the first double-sided adhesive substrate member 24 can correspond in size and shape to the outer perimeter 22 of the flexible plastic member 16 such that when the first double-sided adhesive substrate member 24 is positioned on the flexible plastic member 16 in an orientation maximizing alignment thereof, the outer perimeter 22 of the flexible plastic member 16 extends not more than, for example, 10 mm, 3 mm, or 1 mm beyond the outer perimeter 30 of the first double-sided adhesive substrate member 24 at any point along the outer perimeter 22 of the flexible plastic member 16. Also for example, the outer perimeter 30 of the first double-sided adhesive substrate member 24 can correspond in size and shape to the outer perimeter 22 of the flexible plastic member 16 such that the outer perimeter 30 of the first double-sided adhesive substrate member 24 is identical in size and shape to the outer perimeter 22 of the flexible plastic member 16.

The second face 28 of the first double-sided adhesive substrate member 24 is adhered to the central body portion 18 and the surrounding rim 20 of the flexible plastic member 16. The adhesion can be based, for example, on an adhesive, e.g. a pressure-sensitive adhesive layer, having been applied to the second face 28 of the first double-sided adhesive substrate member 24 and/or to the central body portion 18 and the surrounding rim 20 of the flexible plastic member 16, followed by the second face 28 of the first double-sided adhesive substrate member 24 and the central body portion 18 and the surrounding rim 20 of the flexible plastic member 16 having been placed in contact.

Figure 5:
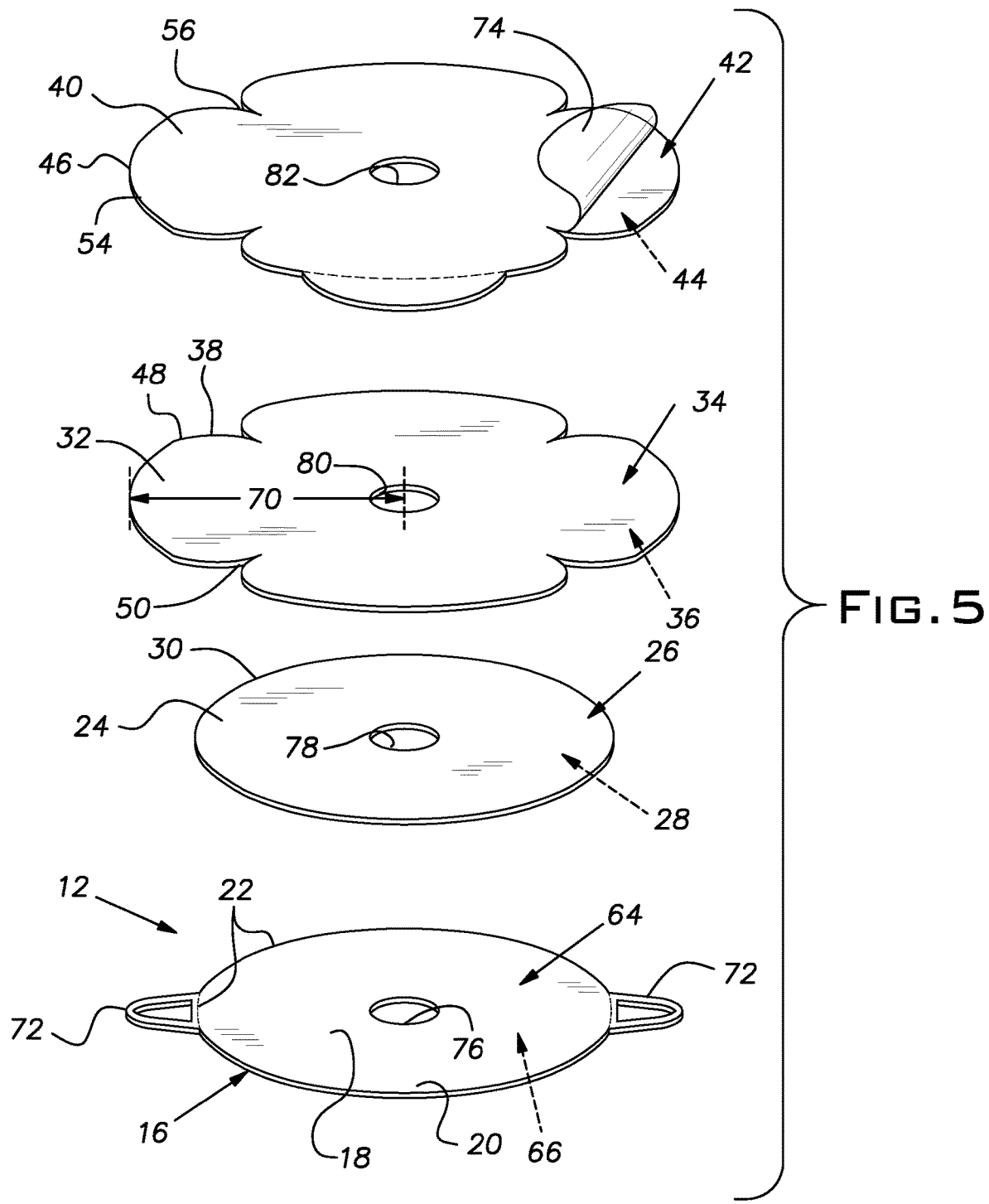
FIG. 5 is an exploded view of another multi-petaled mounting member for an ostomy pouch as disclosed, in which the multi-petaled mounting member is flat.

The multi-petaled outer perimeter 38 of the second double-sided adhesive substrate member 32 has a size greater than the outer perimeter 22 of the flexible plastic member 16 and a shape corresponding to 2 to 8 petals 48 extending radially from the second double-sided adhesive substrate member 32, distributed uniformly around the second double-sided adhesive substrate member 32, and separated by notches 50 that expand radially from the second double-sided adhesive substrate member 32 (FIG. 3, FIG. 4, and FIG. 5).

With respect to size, for example the multi-petaled outer perimeter 38 of the second double-sided adhesive substrate member 32 can have a size greater than the outer perimeter 22 of the flexible plastic member 16 such that when the second double-sided adhesive substrate member 32 is positioned over the flexible plastic member 16 and is centered with respect thereto, the multi-petaled outer perimeter 38 of the second double-sided adhesive substrate member 32 extends at least, for example, 5 to 25 mm, 8 to 20 mm, or 10 to 15 mm, beyond the outer perimeter 22 of the flexible plastic member 16 along at least 50% of the multi-petaled outer perimeter 38 of the second double-sided adhesive substrate member 32 (FIG. 4 and FIG. 5). Also for example, the multi-petaled outer perimeter 38 of the second double-sided adhesive substrate member 32 can have a size greater than the outer perimeter 22 of the flexible plastic member 16 such that when the second double-sided adhesive substrate member 32 is positioned over the flexible plastic member 16 and is centered with respect thereto, the multi-petaled outer perimeter 38 of the second double-sided adhesive substrate member 32 extends at least, for example, 0.2 to 25 mm, 0.5 to 20 mm, or 1 to 15 mm, beyond the outer perimeter 22 of the flexible plastic member 16 along at least 95%, at least 98%, or 100% of the multi-petaled outer perimeter 38 of the second double-sided adhesive substrate member 32.

Figure 6:
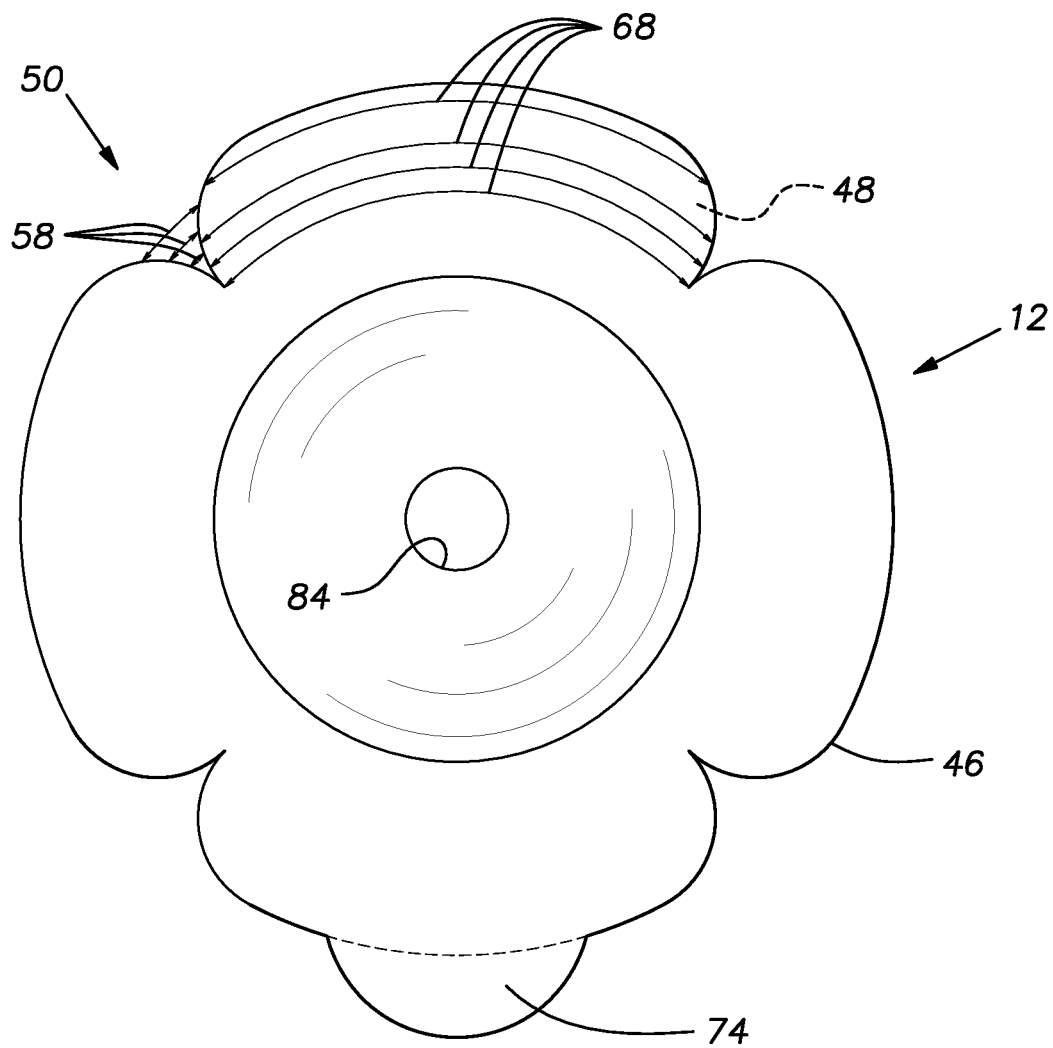
FIG. 6 is a top plan view of a multi-petaled mounting member for an ostomy pouch as disclosed.
Figure 7:
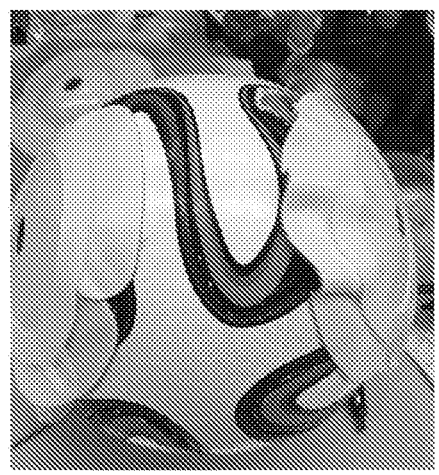
FIG. 7 shows photographs of a multi-petaled mounting member of an ostomy pouch and a circular (non-multi-petaled) mounting member of an ostomy pouch applied to a curved surface of a ball (A) immediately after application and (B) approximately 24 hours after application.
Figure 7:
Figure 8:
FIG. 8 shows photographs of a multi-petaled mounting member of an ostomy pouch and a circular (non-multi-petaled) mounting member of an ostomy pouch applied to a curved surface of a vase (A) immediately after application and (B) approximately 24 hours after application.
Figure 8:
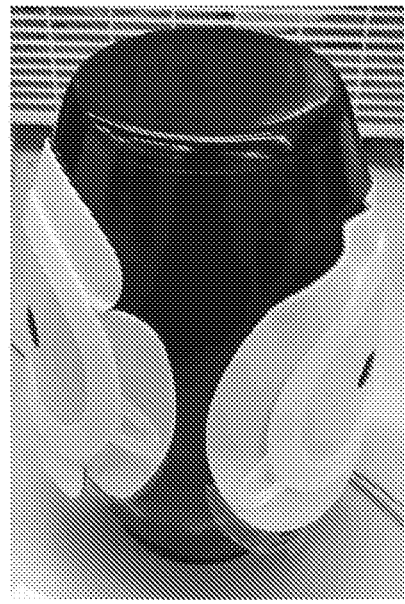
Figure 9:
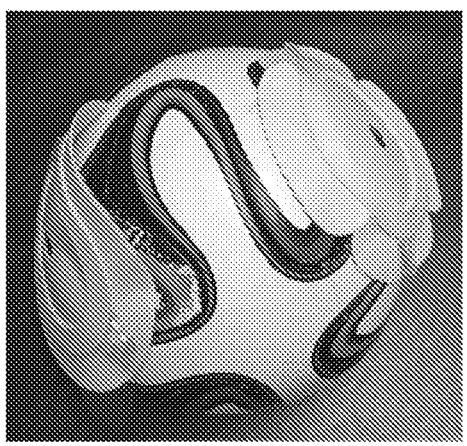
FIG. 9 shows photographs of a multi-petaled mounting member of an ostomy pouch and a circular (non-multi-petaled) mounting member of an ostomy pouch applied to a curved surface of a ball (A) immediately after application and (B) approximately 24 hours after application.
Figure 9:
Figure 10:
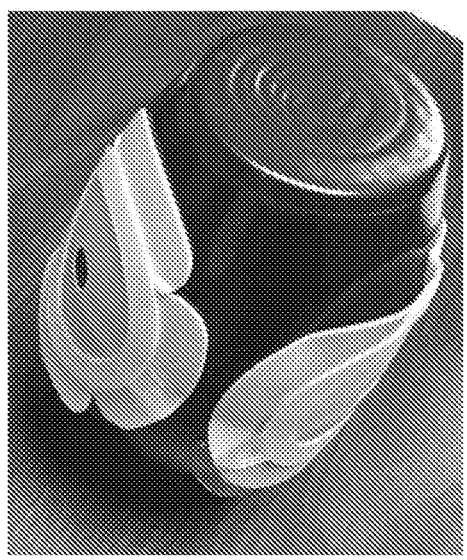
FIG. 10 shows photographs of a multi-petaled mounting member of an ostomy pouch and a circular (non-multi-petaled) mounting member of an ostomy pouch applied to a curved surface of a vase (A) immediately after application and (B) approximately 24 hours after application.
Figure 10:

With respect to shape, for example the multi-petaled outer perimeter 38 of the second double-sided adhesive substrate member 32 can have a shape corresponding to 2 to 8 petals 48 extending radially from the second double-sided adhesive substrate member 32, distributed uniformly around the second double-sided adhesive substrate member 32, and separated by notches 50 that expand radially from the second double-sided adhesive substrate member 32, such that the second double-sided adhesive substrate member 32 has a center, and each of the 2 to 8 petals 48 extend radially with respect to the center of the second double-sided adhesive substrate member 32 (FIG. 4, FIG. 5, and FIG. 6). Also for example, the multi-petaled outer perimeter 38 of the second double-sided adhesive substrate member 32 can have a shape corresponding to 2 to 8 petals 48 extending radially from the second double-sided adhesive substrate member 32, distributed uniformly around the second double-sided adhesive substrate member 32, and separated by notches 50 that expand radially from the second double-sided adhesive substrate member 32, such that each of the 2 to 8 petals 48 is substantially identical in size and that each of the 2 to 8 petals 48 is positioned equidistant from the petals 48 adjacent thereto. Also for example, the multi-petaled outer perimeter 38 of the second double-sided adhesive substrate member 32 can have a shape corresponding to 2 to 8 petals 48 extending radially from the second double-sided adhesive substrate member 32, distributed uniformly around the second double-sided adhesive substrate member 32, and separated by notches 50 that expand radially from the second double-sided adhesive substrate member 32, such that each of the 2 to 8 petals 48 is separated from the petals 48 adjacent thereto by a notch 50 on either side thereof, each notch 50 having a notch width 58, measured as an arcuate length with respect to the center of the second double-sided adhesive substrate member 32, that increases with increasing distance from the center of the second double-sided adhesive substrate member 32.

In some examples, the notches 50 expand radially from the second double-sided adhesive substrate member 32, starting from a distance radially beyond the outer perimeter 22 of the flexible plastic member 16 and the outer perimeter 30 of the first double-sided adhesive substrate member 24, e.g. a distance of 0.5 to 5 mm, 0.8 to 3 mm, or 1 to 2 mm, radially beyond the outer perimeter 22 of the flexible plastic member 16 and the outer perimeter 30 of the first double-sided adhesive substrate member 24 (FIG. 4, FIG. 5, and FIG. 6). In accordance with these examples, during use of the multi-petaled mounting member 12 as adhered to an ostomate, this configuration may provide additional improved fit based on formation of small tears in the second double-sided adhesive substrate member 32, extending from the notches 50 radially inwardly toward the outer perimeter 22 of the flexible plastic member 16 and the outer perimeter 30 of the first double-sided adhesive substrate member 24.

The second face 36 of the second double-sided adhesive substrate member 32 is adhered to the first face 26 of the first double-sided adhesive substrate member 24. Similarly as described above, the adhesion can be based, for example, on an adhesive, e.g. a pressure-sensitive adhesive layer, having been applied to the second face 36 of the second double-sided adhesive substrate member 32 and/or to the first face 26 of the first double-sided adhesive substrate member 24, followed by the second face 36 of the second double-sided adhesive substrate member 32 and the first face 26 of the first double-sided adhesive substrate member 24 having been placed in contact.

The multi-petaled outer perimeter 46 of the adhesive skin barrier member 40 substantially corresponds in size and shape to the multi-petaled outer perimeter 38 of the second double-sided adhesive substrate member 32. Similarly as described above, for example the multi-petaled outer perimeter 46 of the adhesive skin barrier member 40 can correspond in size and shape to the multi-petaled outer perimeter 38 of the second double-sided adhesive substrate member 32 such that when the adhesive skin barrier member 40 is positioned on the second double-sided adhesive substrate member 32 in an orientation maximizing alignment thereof, the multi-petaled outer perimeter 46 of the adhesive skin barrier member 40 extends not more than, for example, 10 mm, 3 mm, or 1 mm beyond the multi-petaled outer perimeter 38 of the second double-sided adhesive substrate member 32 at any point along the multi-petaled outer perimeter 46 of the adhesive skin barrier member 40. Also for example, the multi-petaled outer perimeter 46 of the adhesive skin barrier member 40 can correspond in size and shape to the multi-petaled outer perimeter 38 of the second double-sided adhesive substrate member 32 such that when the adhesive skin barrier member 40 is positioned on the second double-sided adhesive substrate member 32 in an orientation maximizing alignment thereof, the multi-petaled outer perimeter 38 of the second double-sided adhesive substrate member 32 extends not more than, for example, 10 mm, 3 mm, or 1 mm beyond the multi-petaled outer perimeter 46 of the adhesive skin barrier member 40 at any point along the multi-petaled outer perimeter 38 of the second double-sided adhesive substrate member 32. Also for example, the multi-petaled outer perimeter 46 of the adhesive skin barrier member 40 can correspond in size and shape to the multi-petaled outer perimeter 38 of the second double-sided adhesive substrate member 32 such that the multi-petaled outer perimeter 46 of the adhesive skin barrier member 40 is identical in size and shape to the multi-petaled outer perimeter 38 of the second double-sided adhesive substrate member 32. The multi-petaled outer perimeter 46 of the adhesive skin barrier member 40 also has a shape corresponding to 2 to 8 petals 54 extending radially from the adhesive skin barrier member 40, distributed uniformly around the adhesive skin barrier member 40, and separated by notches 56 that expand radially from the adhesive skin barrier member 40.

The second face 44 of the adhesive skin barrier member 40 is adhered to the first face 34 of the second double-sided adhesive substrate member 32. Similarly as described above, the adhesion can be based, for example, on an adhesive, e.g. a pressure-sensitive adhesive layer, having been applied to the second face 44 of the adhesive skin barrier member 40 and/or to the first face 34 of the second double-sided adhesive substrate member 32, followed by the second face 44 of the adhesive skin barrier member 40 and the first face 34 of the second double-sided adhesive substrate member 32 having been placed in contact.

In accordance with some examples, (i) the central body portion 18 of the flexible plastic member 16 has a first face 60 and an opposite second face 62, (ii) the first face 60 of the central body portion 18 is convex, (iii) the second face 62 of the central body portion 18 is concave, and (iv) the second face 28 of the first double-sided adhesive substrate member 24 is adhered to the central body portion 18 on the convex first face 60 of the central body portion 18 (FIG. 3 and FIG. 4). For example, the first face 60 of the central body portion 18 can have a convexity of, for example, 2 to 15 mm, 4 to 12 mm, 5 to 11 mm, or 6 to 10 mm. Also for example, the first face 60 of the central body portion 18 can have a convexity of, for example, 2 mm, 3 mm, 4 mm, 5 mm, 6 mm, 7 mm, 8 mm, 9 mm, 10 mm, 11 mm, 12 mm, 13 mm, 14 mm, or 15 mm. Also for example, the second face 62 of the central body portion 18 can have a concavity complementary to the convexity of the first face 60 of the central body portion 18, e.g. a concavity of 2 to 15 mm, 4 to 12 mm, 5 to 11 mm, or 6 to 10 mm, or of 2 mm, 3 mm, 4 mm, 5 mm, 6 mm, 7 mm, 8 mm, 9 mm, 10 mm, 11 mm, 12 mm, 13 mm, 14 mm, or 15 mm. In accordance with these examples, the central body portion 18 can have a shape of, for example, a spherical cap, e.g. a dome with a rounded top, or a spherical segment, e.g. a dome with a flat top, among other shapes. Also in accordance with these examples, to the extent that the first face 60 of the central body portion 18 is convex, then, following assembly of the multi-petaled mounting member 12, corresponding overlapping portions of the first face 26 of the first double-sided adhesive substrate member 24, the first face 34 of the second double-sided adhesive substrate member 32, and the first face 42 of the adhesive skin barrier member 40 are also convex, and thus then the multi-petaled mounting member 12 is also convex in corresponding portions thereof.

In accordance with other examples, (i) the central body portion 18 of the flexible plastic member 16 has a first face 64 and an opposite second face 66, (ii) the first face 64 of the central body portion 18 is flat, (iii) the second face 66 of the central body portion 18 is flat, and (iv) the second face 28 of the first double-sided adhesive substrate member 24 is adhered to the central body portion 18 on the flat first face 64 of the central body portion 18 (FIG. 3 and FIG. 5). In accordance with these examples, to the extent that the first face 64 of the central body portion 18 is flat, then corresponding overlapping portions of the first face 26 of the first double-sided adhesive substrate member 24, the first face 34 of the second double-sided adhesive substrate member 32, and the first face 42 of the adhesive skin barrier member 40 are also flat, and thus then the multi-petaled mounting member 12 is also flat in corresponding portions thereof.

In accordance with some examples, the 2 to 8 petals 48 each have a petal width 68 that first increases, then decreases, radially outwardly from the second double-sided adhesive substrate member 32 (FIG. 3, FIG. 4, and FIG. 6). For example, the 2 to 8 petals 48 each can have a petal width 68 that first increases, then decreases, radially outwardly from the second double-sided adhesive substrate member 32, such that the second double-sided adhesive substrate member 32 has a center, and the 2 to 8 petals 48 each have a petal width 68, measured as an arcuate length with respect to the center of the second double-sided adhesive substrate member 32, that first increases, then decreases, with increasing distance from the center of the second double-sided adhesive substrate member 32. In accordance with these examples, the 2 to 8 petals 54 are also dimensioned this way.

Also in accordance with some examples, the second double-sided adhesive substrate member 32 has a maximum radius 70, and at least 50% of the multi-petaled outer perimeter 38 of the second double-sided adhesive substrate member 32 extends to the maximum radius 70 of the second double-sided adhesive substrate member 32 (FIG. 3 and FIG. 4). For example, the second double-sided adhesive substrate member 32 can have a maximum radius 70, and at least 50% of the multi-petaled outer perimeter 38 of the second double-sided adhesive substrate member 32 can extend to the maximum radius 70 of the second double-sided adhesive substrate member 32, such that, for example, at least 50%, 60%, 70% or 80% of the multi-petaled outer perimeter 38 of the second double-sided adhesive substrate member 32 extends to the same distance from the center of the second double-sided adhesive substrate member 32, and no point on the outer perimeter 38 of the second double-sided adhesive substrate member 32 extends further than this. In accordance with these examples, the adhesive skin barrier member 40 is also dimensioned this way.

Also in accordance with some examples, the shape of the multi-petaled outer perimeter 38 of the second double-sided adhesive substrate member 32 corresponds to 3 to 6 petals 48. For example, the shape of the multi-petaled outer perimeter 38 of the second double-sided adhesive substrate member 32 can correspond, for example, to 3 petals 48, 4 petals 48, 5 petals 48, or 6 petals 48. In accordance with these examples, the shape of the multi-petaled outer perimeter 46 of the adhesive skin barrier member 40 is also dimensioned this way.

Also in accordance with some examples, the surrounding rim 20 of the flexible plastic member 16 is substantially annular. For example, the surrounding rim 20 of the flexible plastic member 16 can be circular. In other examples, the surrounding rim 20 of the flexible plastic member 16 can have other shapes, e.g. oval, polygonal, etc.

Also in accordance with some examples, the flexible plastic member 16 further comprises mounting loops 72 that are diametrically opposed and that extend radially outwardly from the surrounding rim 20 to no further than the multi-petaled outer perimeter 38 of the second double-sided adhesive substrate member 32 and the multi-petaled outer perimeter 46 of the adhesive skin barrier member 40 (FIG. 2, FIG. 3, and FIG. 4). The mounting loops 72 can be used, for example, for mounting the multi-petaled mounting member 12 to an ostomy belt (not shown).

Also in accordance with some examples, the adhesive skin barrier member 40 comprises an elastomer hydrocolloid mixture. The elastomer hydrocolloid mixture can include, for example, a Karaya-glycerine formulation, mixtures of polyacrylamide resins, and/or other polyols.

Also in accordance with some examples, the multi-petaled mounting member 12 further comprises a removable protective film 74, wherein the removable protective film 74 covers the first face 42 of the adhesive skin barrier member 40 (FIG. 3 and FIG. 4). In some examples, the removable protective film 74 can include a part, such as a tab, that extends continuously beyond the multi-petaled outer perimeter 38 of the second double-sided adhesive substrate member 32 and the multi-petaled outer perimeter 46 of the adhesive skin barrier member 40, and that can be used to remove the removable protective film 74 from the first face 42 of the adhesive skin barrier member 40.

Also in accordance with some examples, each of the flexible plastic member 16, the first double-sided adhesive substrate member 24, the second double-sided adhesive substrate member 32, and the adhesive skin barrier member 40 have a stoma inlet portal 76, 78, 80, 82, respectively, centrally positioned and extending therethrough, which together form a stoma inlet portal 84 of the multi-petaled mounting member 12. The stoma inlet portals 76, 78, 80, 82 of the flexible plastic member 16, the first double-sided adhesive substrate member 24, the second double-sided adhesive substrate member 32, and the adhesive skin barrier member 40, respectively, can have a size and shape suitable for a stoma of an ostomate. For example, the stoma inlet portals 76, 78, 80, 82 can have a size corresponding to a diameter of, for example, 10 mm to 50 mm, e.g. about 12 to 13 mm, about 15 to 16 mm, about 22 to 23 mm, about 25 to 26 mm, about 28 to 29 mm, about 31 to 32 mm, about 34 to 35 mm, about 38 to 39 mm, about 41 to 42 mm, or about 44 to 45 mm. Also for example, the stoma inlet portals 76, 78, 80, 82 can have a size corresponding to a diameter of, for example, 12.7 mm, 15.9 mm, 22.2 mm, 25.4 mm, 28.6 mm, 31.8 mm, 34.9 mm, 41.3 mm, or 44.5 mm. Also for example, the stoma inlet portals 76, 78, 80, 82 can have a shape corresponding to a circle. Also for example, the stoma inlet portals 76, 78, 80, 82 can have a shape that is cut to fit a stoma of an ostomate.

The multi-petaled mounting member 12 can be assembled as follows. A pressure-sensitive adhesive layer is applied to each of the first face 26 of the first double-sided adhesive substrate member 24, the second face 28 of the first double-sided adhesive substrate member 24, and the first face 34 of the second double-sided adhesive substrate member 32. For ease of handling during assembly, the pressure-sensitive adhesive layers are respectively covered by protective liners.

The protective liner is removed from the pressure-sensitive adhesive layer of the first face 26 of the first double-sided adhesive substrate member 24. The first double-sided adhesive substrate member 24 is centered with respect to the second double-sided adhesive substrate member 32. The pressure-sensitive adhesive layer of the first face 26 of the first double-sided adhesive substrate member 24 is adhered to the second face 36 of the second double-sided adhesive substrate member 32. To aid in assembly, pilot apertures can be provided at centers of the first double-sided adhesive substrate member 24 and the second double-sided adhesive substrate member 32. After the first double-sided adhesive substrate member 24 and the second double-sided adhesive substrate member 32 are assembled, the protective liner is removed from the pressure-sensitive adhesive layer of the first face 34 of the second double-sided adhesive substrate member 32. The second double-sided adhesive substrate member 32 is centered with respect to the adhesive skin barrier member 40. The pressure-sensitive adhesive layer of the first face 34 of the second double-sided adhesive substrate member 32 is adhered to the second face 44 of the adhesive skin barrier member 40. To aid in assembly, a pilot aperture can be provided at the center of the adhesive skin barrier member 40. After the first double-sided adhesive substrate member 24, the second double-sided adhesive substrate member 32, and the adhesive skin barrier member 40 are assembled, the protective liner is removed from the pressure-sensitive adhesive layer of second face 28 of the first double-sided adhesive substrate member 24. The first double-sided adhesive substrate member 24 is centered with respect to the flexible plastic member 16. The pressure-sensitive adhesive layer of the second face 28 of the first double-sided adhesive substrate member 24 is adhered to a face of the flexible plastic member 16, including the central body portion 18 and the surrounding rim 20. To aid in assembly, a pilot aperture can be provided at the center of the flexible plastic member 16. Heat and pressure are applied to an annular zone z (FIG. 3) of the resulting assembly including the surrounding rim 20 of the flexible plastic member 16 and/or portions of the first double-sided adhesive substrate member 24, the second double-sided adhesive substrate member 32, and the adhesive skin barrier member 40 overlaying the surrounding rim 20 of the flexible plastic member 16. The multi-petaled mounting member 12 also can be assembled by other methods.

An ostomy appliance 52 also is disclosed (FIG. 2). The ostomy appliance 52 comprises a multi-petaled mounting member 12. The ostomy appliance 52 also comprises an ostomy pouch 14.

The multi-petaled mounting member 12 is as described above. Accordingly, the multi-petaled mounting member 12 comprises (a) a flexible plastic member 16 comprising a central body portion 18, a surrounding rim 20, and an outer perimeter 22, (b) a first double-sided adhesive substrate member 24 comprising a first face 26, an opposite second face 28, and an outer perimeter 30, (c) a second double-sided adhesive substrate member 32 comprising a first face 34, an opposite second face 36, and a multi-petaled outer perimeter 38, and (d) an adhesive skin barrier member 40 comprising a first face 42, an opposite second face 44, and a multi-petaled outer perimeter 46 (FIG. 3 and FIG. 4). The outer perimeter 30 of the first double-sided adhesive substrate member 24 substantially corresponds in size and shape to the outer perimeter 22 of the flexible plastic member 16. The second face 28 of the first double-sided adhesive substrate member 24 is adhered to the central body portion 18 and the surrounding rim 20 of the flexible plastic member 16. The multi-petaled outer perimeter 38 of the second double-sided adhesive substrate member 32 has a size greater than the outer perimeter 22 of the flexible plastic member 16 and a shape corresponding to 2 to 8 petals 48 extending radially from the second double-sided adhesive substrate member 32, distributed uniformly around the second double-sided adhesive substrate member 32, and separated by notches 50 that expand radially from the second double-sided adhesive substrate member 32. The second face 36 of the second double-sided adhesive substrate member 32 is adhered to the first face 26 of the first double-sided adhesive substrate member 24. The multi-petaled outer perimeter 46 of the adhesive skin barrier member 40 substantially corresponds in size and shape to the multi-petaled outer perimeter 38 of the second double-sided adhesive substrate member 32. The second face 44 of the adhesive skin barrier member 40 is adhered to the first face 34 of the second double-sided adhesive substrate member 32.

The ostomy pouch 14 comprises a proximal sheet 86 of plastic film and a distal sheet 88 of plastic film, the proximal sheet 86 and the distal sheet 88 being sealed at their respective peripheries to form the ostomy pouch 14 (FIG. 2 and FIG. 3). The proximal sheet 86 comprises a stoma inlet portal 90 having an inner perimeter 92 and a zone 94 surrounding the inner perimeter. The surrounding rim 20 of the flexible plastic member 16 further comprises an inner perimeter 96. The inner perimeter 96 of the surrounding rim 20 of the flexible plastic member 16 substantially corresponds in size and shape to the inner perimeter 92 of the stoma inlet portal 90 of the proximal sheet 86. The surrounding rim 20 of the flexible plastic member 16 is sealed to the zone surrounding the inner perimeter 92 of the stoma inlet portal 90 of the proximal sheet 86.

The ostomy pouch can be designed for single use, e.g. by not having an opening for draining contents of the ostomy pouch, or for multiple use, e.g. by having an opening for draining contents of the ostomy pouch.

The ostomy appliance 52 can be made as follows. The multi-petaled mounting member 12 is placed on a sheet of plastic film, which will become the proximal sheet 86 of the ostomy pouch 14. The multi-petaled mounting member 12 is placed over the stoma inlet portal 90 of the proximal sheet 86. The proximal sheet 86 can be covered with a cloth-like porous material for the comfort of the ostomate. Pilot apertures provided in the centers of each of the flexible plastic member 16, the first double-sided adhesive substrate member 24, the second double-sided adhesive substrate member 32, and the adhesive skin barrier member 40 are die cut to form properly sized stoma inlet portals 76, 78, 80, 82, respectively, in each. Heat and pressure are applied to the annular zone z (FIG. 3) of the resulting assembly including the surrounding rim 20 of the flexible plastic member 16 and/or portions of the first double-sided adhesive substrate member 24, the second double-sided adhesive substrate member 32, and the adhesive skin barrier member 40 overlaying the surrounding rim 20 of the flexible plastic member 16, thereby sealing the surrounding rim 20 of the flexible plastic member 16 to the proximal sheet 86. The proximal sheet 86 is backed with another sheet of plastic film, which will become the distal sheet 88 of the ostomy pouch 14. The ostomy pouch 14 is then formed by die-cutting the proximal sheet 86 and the distal sheet 88 along a line, followed by heat sealing along the line.

Also disclosed is a method of adhering an ostomy appliance 52 to an ostomate at a peristomal skin surface of the ostomate (FIG. 2). In accordance with the method, the ostomy appliance 52 comprises a multi-petaled mounting member 12. The ostomy appliance 52 also comprises an ostomy pouch 14.

The multi-petaled mounting member 12 is as described above. Accordingly, the multi-petaled mounting member 12 comprises (a) a flexible plastic member 16 comprising a central body portion 18, a surrounding rim 20, and an outer perimeter 22, (b) a first double-sided adhesive substrate member 24 comprising a first face 26, an opposite second face 28, and an outer perimeter 30, (c) a second double-sided adhesive substrate member 32 comprising a first face 34, an opposite second face 36, and a multi-petaled outer perimeter 38, and (d) an adhesive skin barrier member 40 comprising a first face 42, an opposite second face 44, and a multi-petaled outer perimeter 46 (FIG. 3 and FIG. 4). The outer perimeter 30 of the first double-sided adhesive substrate member 24 substantially corresponds in size and shape to the outer perimeter 22 of the flexible plastic member 16. The second face 28 of the first double-sided adhesive substrate member 24 is adhered to the central body portion 18 and the surrounding rim 20 of the flexible plastic member 16. The multi-petaled outer perimeter 38 of the second double-sided adhesive substrate member 32 has a size greater than the outer perimeter 22 of the flexible plastic member 16 and a shape corresponding to 2 to 8 petals 48 extending radially from the second double-sided adhesive substrate member 32, distributed uniformly around the second double-sided adhesive substrate member 32, and separated by notches 50 that expand radially from the second double-sided adhesive substrate member 32. The second face 36 of the second double-sided adhesive substrate member 32 is adhered to the first face 26 of the first double-sided adhesive substrate member 24. The multi-petaled outer perimeter 46 of the adhesive skin barrier member 40 substantially corresponds in size and shape to the multi-petaled outer perimeter 38 of the second double-sided adhesive substrate member 32. The second face 44 of the adhesive skin barrier member 40 is adhered to the first face 34 of the second double-sided adhesive substrate member 32.

The multi-petaled mounting member 12 further comprises a removable protective film 74, wherein the removable protective film 74 covers the first face 42 of the adhesive skin barrier member 40. Again, in some examples, the removable protective film 74 can include a part, such as a tab, that extends continuously beyond the multi-petaled outer perimeter 38 of the second double-sided adhesive substrate member 32 and the multi-petaled outer perimeter 46 of the adhesive skin barrier member 40, and that can be used to remove the removable protective film 74 from the first face 42 of the adhesive skin barrier member 40.

Each of the flexible plastic member 16, the first double-sided adhesive substrate member 24, the second double-sided adhesive substrate member 32, and the adhesive skin barrier member 40 have a stoma inlet portal 76, 78, 80, 82, respectively, centrally positioned and extending therethrough.

The ostomy pouch 14 comprises a proximal sheet 86 of plastic film and a distal sheet 88 of plastic film, the proximal sheet 86 and the distal sheet 88 being sealed at their respective peripheries to form the ostomy pouch 14 (FIG. 2 and FIG. 3). The proximal sheet 86 comprises a stoma inlet portal 90 having an inner perimeter 92 and a zone 94 surrounding the inner perimeter. The surrounding rim 20 of the flexible plastic member 16 further comprises an inner perimeter 96. The inner perimeter 96 of the surrounding rim 20 of the flexible plastic member 16 substantially corresponds in size and shape to the inner perimeter 92 of the stoma inlet portal 90 of the proximal sheet 86. The surrounding rim 20 of the flexible plastic member 16 is sealed to the zone surrounding the inner perimeter 92 of the stoma inlet portal 90 of the proximal sheet 86.

The method comprises a step of (1) removing the removable protective film 74 from the first face 42 of the adhesive skin barrier member 40 (FIG. 4). This exposes the first face 42 of the adhesive skin barrier member 40.

The method also comprises a step of (2) placing the first face 42 of the adhesive skin barrier member 40 at the peristomal region of the ostomate, such that the stoma inlet portal 90 of the proximal sheet 86 of the ostomy pouch 14 and the stoma inlet portals 76, 78, 80, 82 of the flexible plastic member 16, the first double-sided adhesive substrate member 24, the second double-sided adhesive substrate member 32, and the adhesive skin barrier member 40, respectively, are aligned with a stoma of the ostomate. In accordance with the method, the ostomy appliance 52 is thereby adhered to the ostomate at the peristomal skin surface of the ostomate (FIG. 2, FIG. 3, and FIG. 4).

In accordance with some examples, the ostomy appliance 52 adheres to the ostomate at the peristomal skin surface of the ostomate with a smooth fit. For example, the ostomy appliance 52 can adhere to the ostomate at the peristomal skin surface of the ostomate with a smooth fit such that the multi-petaled mounting member 12 is adapted to the peristomal skin surface of the ostomate, without undesirable bunching upon application. Also for example, the ostomy appliance 52 can adhere to the ostomate at the peristomal skin surface of the ostomate with a smooth fit across a range of peristomal skin surface contours of ostomates, e.g. for ostomates with peristomal skin surfaces that are flat, curved, bulging, and/or irregular. As the pouch fills with body waste, the adhesive skin barrier member 40 will remain secure and stay attached at the peristomal skin surface of the ostomate, and not peel away.

Also in accordance with some examples, the ostomy appliance 52 adheres to the ostomate at the peristomal skin surface of the ostomate without application of adhesive tape to the ostomy appliance 52 or to the ostomate. For example, the ostomy appliance 52 can adhere to the ostomate at the peristomal skin surface of the ostomate without application of adhesive tape to the ostomy appliance 52 or to the ostomate such that no adhesive tape needs to be applied to smooth, press, or adhere the mounting member to the skin at and adjacent the peristomal skin surface of the ostomate. Also for example, the ostomy appliance 52 can adhere to the ostomate at the peristomal skin surface of the ostomate without application of adhesive tape to the ostomy appliance 52 or to the ostomate across a range of peristomal skin surface contours of ostomates, e.g. for ostomates with peristomal skin surfaces that are flat, curved, bulging, and/or irregular. Again, as the pouch fills with body waste, the adhesive skin barrier member 40 will remain secure and stay attached at the peristomal skin surface of the ostomate, and not peel away.

In accordance with some examples, (i) the central body portion 18 of the flexible plastic member 16 has a first face 60 and an opposite second face 62, (ii) the first face 60 of the central body portion 18 is convex, (iii) the second face 62 of the central body portion 18 is concave, and (iv) the second face 28 of the first double-sided adhesive substrate member 24 is adhered to the central body portion 18 on the convex first face 60 of the central body portion 18.

Also in accordance with some examples, (i) the central body portion 18 of the flexible plastic member 16 has a first face 64 and an opposite second face 66, (ii) the first face 64 of the central body portion 18 is flat, (iii) the second face 66 of the central body portion 18 is flat, and (iv) the second face 28 of the first double-sided adhesive substrate member 24 is adhered to the central body portion 18 on the flat first face 64 of the central body portion 18.

Also in accordance with some examples, the 2 to 8 petals 48 each have a petal width 68 that first increases, then decreases, radially outwardly from the second double-sided adhesive substrate member 32.

Also in accordance with some examples, the second double-sided adhesive substrate member 32 has a maximum radius 70, and at least 50% of the multi-petaled outer perimeter 38 of the second double-sided adhesive substrate member 32 extends to the maximum radius 70 of the second double-sided adhesive substrate member 32.

Also in accordance with some examples, the shape of the multi-petaled outer perimeter 38 of the second double-sided adhesive substrate member 32 corresponds to 3 to 6 petals 48.

Also in accordance with some examples, the surrounding rim 20 of the flexible plastic member 16 is substantially annular.

Also in accordance with some examples, the flexible plastic member 16 further comprises mounting loops 72 that are diametrically opposed and that extend radially outwardly from the surrounding rim 20 to no further than the multi-petaled outer perimeter 38 of the second double-sided adhesive substrate member 32 and the multi-petaled outer perimeter 46 of the adhesive skin barrier member 40.

Also in accordance with some examples, the adhesive skin barrier member 40 comprises an elastomer hydrocolloid mixture.

Also disclosed is another method of adhering an ostomy appliance 52 to an ostomate at a peristomal skin surface of the ostomate (FIG. 2). In accordance with the method, the ostomy appliance 52 comprises a multi-petaled mounting member 12. The ostomy appliance 52 also comprises an ostomy pouch 14.

The multi-petaled mounting member 12 is as described above. Accordingly, the multi-petaled mounting member 12 comprises (a) a flexible plastic member 16 comprising a central body portion 18, a surrounding rim 20, and an outer perimeter 22, (b) a first double-sided adhesive substrate member 24 comprising a first face 26, an opposite second face 28, and an outer perimeter 30, (c) a second double-sided adhesive substrate member 32 comprising a first face 34, an opposite second face 36, and a multi-petaled outer perimeter 38, and (d) an adhesive skin barrier member 40 comprising a first face 42, an opposite second face 44, and a multi-petaled outer perimeter 46 (FIG. 3 and FIG. 4). The outer perimeter 30 of the first double-sided adhesive substrate member 24 substantially corresponds in size and shape to the outer perimeter 22 of the flexible plastic member 16. The second face 28 of the first double-sided adhesive substrate member 24 is adhered to the central body portion 18 and the surrounding rim 20 of the flexible plastic member 16. The multi-petaled outer perimeter 38 of the second double-sided adhesive substrate member 32 has a size greater than the outer perimeter 22 of the flexible plastic member 16 and a shape corresponding to 2 to 8 petals 48 extending radially from the second double-sided adhesive substrate member 32, distributed uniformly around the second double-sided adhesive substrate member 32, and separated by notches 50 that expand radially from the second double-sided adhesive substrate member 32. The second face 36 of the second double-sided adhesive substrate member 32 is adhered to the first face 26 of the first double-sided adhesive substrate member 24. The multi-petaled outer perimeter 46 of the adhesive skin barrier member 40 substantially corresponds in size and shape to the multi-petaled outer perimeter 38 of the second double-sided adhesive substrate member 32. The second face 44 of the adhesive skin barrier member 40 is adhered to the first face 34 of the second double-sided adhesive substrate member 32.

The multi-petaled mounting member 12 further comprises a removable protective film 74, wherein the removable protective film 74 covers the first face 42 of the adhesive skin barrier member 40. Again, in some examples, the removable protective film 74 can include a part, such as a tab, that extends continuously beyond the multi-petaled outer perimeter 38 of the second double-sided adhesive substrate member 32 and the multi-petaled outer perimeter 46 of the adhesive skin barrier member 40, and that can be used to remove the removable protective film 74 from the first face 42 of the adhesive skin barrier member 40.

The ostomy pouch 14 comprises a proximal sheet 86 of plastic film and a distal sheet 88 of plastic film, the proximal sheet 86 and the distal sheet 88 being sealed at their respective peripheries to form the ostomy pouch 14 (FIG. 2 and FIG. 3). The proximal sheet 86 comprises a stoma inlet portal 90 having an inner perimeter 92 and a zone 94 surrounding the inner perimeter. The surrounding rim 20 of the flexible plastic member 16 further comprises an inner perimeter 96. The inner perimeter 96 of the surrounding rim 20 of the flexible plastic member 16 substantially corresponds in size and shape to the inner perimeter 92 of the stoma inlet portal 90 of the proximal sheet 86. The surrounding rim 20 of the flexible plastic member 16 is sealed to the zone surrounding the inner perimeter 92 of the stoma inlet portal 90 of the proximal sheet 86.

The method comprises a step of (1) removing the removable protective film 74 from the first face 42 of the adhesive skin barrier member 40 (FIG. 4). The method also comprises a step of (2) cutting a hole, centrally positioned, through at least the adhesive skin barrier member 40, such that each of the flexible plastic member 16, the first double-sided adhesive substrate member 24, the second double-sided adhesive substrate member 32, and the adhesive skin barrier member 40 have a stoma inlet portal 76, 78, 80, 82, respectively, centrally positioned and extending therethrough (FIG. 2, FIG. 3, and FIG. 4). The method also comprises a step of (3) placing the first face 42 of the adhesive skin barrier member 40 at the peristomal region of the ostomate, such that the stoma inlet portal 90 of the proximal sheet 86 of the ostomy pouch 14 and the stoma inlet portals 76, 78, 80, 82 of the flexible plastic member 16, the first double-sided adhesive substrate member 24, the second double-sided adhesive substrate member 32, and the adhesive skin barrier member 40, respectively, are aligned with a stoma of the ostomate. In accordance with the method, the ostomy appliance 52 is thereby adhered to the ostomate at the peristomal skin surface of the ostomate.

In some examples, the ostomy appliance 52 adheres to the ostomate at the peristomal skin surface of the ostomate with a smooth fit.

Also in some examples, the ostomy appliance 52 adheres to the ostomate at the peristomal skin surface of the ostomate without application of adhesive tape to the ostomy appliance 52 or to the ostomate.

In accordance with some examples, (i) the central body portion 18 of the flexible plastic member 16 has a first face 60 and an opposite second face 62, (ii) the first face 60 of the central body portion 18 is convex, (iii) the second face 62 of the central body portion 18 is concave, and (iv) the second face 28 of the first double-sided adhesive substrate member 24 is adhered to the central body portion 18 on the convex first face 60 of the central body portion 18.

Also in accordance with some examples, (i) the central body portion 18 of the flexible plastic member 16 has a first face 64 and an opposite second face 66, (ii) the first face 64 of the central body portion 18 is flat, (iii) the second face 66 of the central body portion 18 is flat, and (iv) the second face 28 of the first double-sided adhesive substrate member 24 is adhered to the central body portion 18 on the flat first face 64 of the central body portion 18.

Also in accordance with some examples, the 2 to 8 petals 48 each have a petal width 68 that first increases, then decreases, radially outwardly from the second double-sided adhesive substrate member 32.

Also in accordance with some examples, the second double-sided adhesive substrate member 32 has a maximum radius 70, and at least 50% of the multi-petaled outer perimeter 38 of the second double-sided adhesive substrate member 32 extends to the maximum radius 70 of the second double-sided adhesive substrate member 32.

Also in accordance with some examples, the shape of the multi-petaled outer perimeter 38 of the second double-sided adhesive substrate member 32 corresponds to 3 to 6 petals 48.

Also in accordance with some examples, the surrounding rim 20 of the flexible plastic member 16 is substantially annular.

Also in accordance with some examples, the flexible plastic member 16 further comprises mounting loops 72 that are diametrically opposed and that extend radially outwardly from the surrounding rim 20 to no further than the multi-petaled outer perimeter 38 of the second double-sided adhesive substrate member 32 and the multi-petaled outer perimeter 46 of the adhesive skin barrier member 40.

Also in accordance with some examples, the adhesive skin barrier member 40 comprises an elastomer hydrocolloid mixture.

EXAMPLES

Comparisons of surface adhesion by multi-petaled mounting members for an ostomy pouch versus circular (i.e. non-multi-petaled) mounting members for an ostomy pouch were carried out. The comparisons involved the following steps. First, a multi-petaled mounting member and a circular mounting member were applied to a curved surface of an object, such that most of each mounting member was pressed by hand to the curved surface. Next, it was observed whether the application of each mounting member had been accomplished with a smooth fit or whether undesirable bunching had occurred. Then the object was kept at approximately 24° C. for approximately 24 hours. Finally, it was observed whether peeling of either of the mounting members from the curved surface of the object had occurred where each mounting member had been pressed by hand to the curved surface.

Two objects were used, a ball and a vase. The ball had a curved surface corresponding to a round surface. The vase had a curved surface corresponding to a convex surface. The curved surfaces were analogous to peristomal skin surfaces of ostomates, such as, for example, a curved abdominal surface associated with an ostomate who is overweight and, also for example, a curved abdominal surface associated with an ostomate who is bending at the waist. The multi-petaled mounting members and the circular mounting members both included the same adhesive, corresponding to an elastomer hydrocolloid mixture that is used commercially on mounting members of ostomy appliances. The adhesive is not specific to skin and would be expected to accomplish adhesion similarly for the ball and the vase as for skin.

For these comparisons, surface adhesion by the multi-petaled mounting members and the circular mounting members was tested without ostomy pouches attached to the mounting members. This was because the comparisons were focused on adhesion of the mounting members to the curved surfaces of the ball and the vase, and attachment of ostomy pouches to the mounting members would have obscured views of the mounting members as adhered to the curved surfaces.

Results of four comparisons are shown in FIG. 7, FIG. 8, FIG. 9, and FIG. 10.

In a first comparison, following application of a multi-petaled mounting member and a circular mounting member to the curved surface of the ball, such that most of each mounting member was pressed by hand to the curved surface, it was observed that application of the multi-petaled mounting member had been accomplished with a smooth fit (FIG. 7A, left side, top half), whereas undesirable bunching had occurred upon application of the circular mounting member (FIG. 7A, right side, top half). Also, after the ball had been kept at approximately 24° C. for approximately 24 hours, it was observed that no peeling of the multi-petaled mounting member from the ball had occurred where the multi-petaled mounting member had been pressed by hand to the curved surface (FIG. 7B, right side, top half), whereas peeling of the circular mounting member from the ball had occurred where the circular mounting member had been pressed by hand to the curved surface (FIG. 7B, left side, top half).

Similarly, in a second comparison, following application of a multi-petaled mounting member and a circular mounting member to the curved surface of the vase, such that most of each mounting member was pressed by hand to the curved surface, it was observed that application of the multi-petaled mounting member had been accomplished with a smooth fit (FIG. 8A, left side, top half), whereas undesirable bunching had occurred upon application of the circular mounting member (FIG. 8A, right side, top half). Also, after the vase had been kept at approximately 24° C. for approximately 24 hours, it was observed that no peeling of the multi-petaled mounting member from the vase had occurred where the multi-petaled mounting member had been pressed by hand to the curved surface (FIG. 8B, left side, top half), whereas peeling of the circular mounting member from the vase had occurred where the circular mounting member had been pressed by hand to the curved surface (FIG. 8B, right side, top half).

Like the first comparison, in a third comparison, following application of a multi-petaled mounting member and a circular mounting member to the curved surface of the ball, such that most of each mounting member was pressed by hand to the curved surface, it was observed that application of the multi-petaled mounting member had been accomplished with a smooth fit (FIG. 9A, right side, top half), whereas undesirable bunching had occurred upon application of the circular mounting member (FIG. 9A, left side, top half). Also, after the ball had been kept at approximately 24° C. for approximately 24 hours, it was observed that no peeling of the multi-petaled mounting member from the ball had occurred where the multi-petaled mounting member had been pressed by hand to the curved surface (FIG. 9B, right side, bottom half), whereas peeling of the circular mounting member from the ball had occurred where the circular mounting member had been pressed by hand to the curved surface (FIG. 9B, left side, top half).

Also, like the second comparison, in a fourth comparison, following application of a multi-petaled mounting member and a circular mounting member to the curved surface of the vase, such that most of each mounting member was pressed by hand to the curved surface, it was observed that application of the multi-petaled mounting member had been accomplished with a smooth fit (FIG. 10A, left side, top half), whereas undesirable bunching had occurred upon application of the circular mounting member (FIG. 10A, right side, top half). Also, after the vase had been kept at approximately 24° C. for approximately 24 hours, it was observed that no peeling of the multi-petaled mounting member from the vase had occurred where the multi-petaled mounting member had been pressed by hand to the curved surface (FIG. 10B, left side, top half), whereas peeling of the circular mounting member from the vase had occurred where the circular mounting member had been pressed by hand to the curved surface (FIG. 10B, right side, top half).

The results demonstrate that a multi-petaled mounting member for an ostomy pouch can adhere to curved surfaces analogous to peristomal skin surfaces of ostomates with a smooth fit, without undesirable bunching upon application and across a range of surface contours, consistent with an ostomy appliance comprising the multi-petaled mounting member doing the same. The results also demonstrate that a multi-petaled mounting member for an ostomy pouch can adhere to curved surfaces analogous to peristomal skin surfaces of ostomates without application of adhesive tape to the multi-petaled mounting member or the curved surfaces, such that no adhesive tape needs to be applied to smooth, press, or adhere the mounting member to the surface and across a range of surface contours, also consistent with an ostomy appliance comprising the multi-petaled mounting member doing the same. Based on these results, it is believed that the multi-petaled mounting member can provide longer wear times relative to the circular mounting member, e.g. wear times of 3 to 5 days versus wear times of several hours to half of a day, particularly as a corresponding ostomy pouch fills with body waste and the weight of the ostomy pouch thus increases.

INDUSTRIAL APPLICABILITY

The multi-petaled mounting member for an ostomy pouch and the ostomy appliance disclosed herein are useful for collection of waste from surgically diverted organs of ostomates.

The invention claimed is:

1. A multi-petaled mounting member for an ostomy pouch comprising:
   (a) a flexible plastic member comprising a central body portion, a surrounding rim, and an outer perimeter,
   (b) a first double-sided adhesive substrate member comprising a first face, an opposite second face, and an outer perimeter, wherein (i) the outer perimeter of the first double-sided adhesive substrate member substantially corresponds in size and shape to the outer perimeter of the flexible plastic member, and (ii) the second face of the first double-sided adhesive substrate member is adhered to the central body portion and the surrounding rim of the flexible plastic member,
   (c) a second double-sided adhesive substrate member comprising a first face, an opposite second face, and a multi-petaled outer perimeter, wherein (i) the multi-petaled outer perimeter of the second double-sided adhesive substrate member has a size greater than the outer perimeter of the flexible plastic member and a shape corresponding to 2 to 8 petals extending radially from the second double-sided adhesive substrate member, distributed uniformly around the second double-sided adhesive substrate member, and separated by notches that expand radially from the second double-sided adhesive substrate member, wherein each of the 2 to 8 petals intersects angularly with each petal adjacent thereto, thereby defining the notches, and (ii) the second face of the second double-sided adhesive substrate member is adhered to the first face of the first double-sided adhesive substrate member, and
   (d) an adhesive skin barrier member comprising a first face, an opposite second face, and a multi-petaled outer perimeter, wherein (i) the multi-petaled outer perimeter of the adhesive skin barrier member substantially corresponds in size and shape to the multi-petaled outer perimeter of the second double-sided adhesive substrate member, and (ii) the second face of the adhesive skin barrier member is adhered to the first face of the second double-sided adhesive substrate member;
   wherein the 2 to 8 petals each have a width that first increases, then decreases, radially outwardly from the second double-sided adhesive substrate member.

2. The multi-petaled mounting member of claim 1, wherein: (i) the central body portion of the flexible plastic member has a first face and an opposite second face, (ii) the first face of the central body portion is convex, (iii) the second face of the central body portion is concave, and (iv) the second face of the first double-sided adhesive substrate member is adhered to the central body portion on the convex first face of the central body portion.

3. The multi-petaled mounting member of claim 1, wherein: (i) the central body portion of the flexible plastic member has a first face and an opposite second face, (ii) the first face of the central body portion is flat, (iii) the second face of the central body portion is flat, and (iv) the second face of the first double-sided adhesive substrate member is adhered to the central body portion on the flat first face of the central body portion.

4. The multi-petaled mounting member of claim 1, wherein the second double-sided adhesive substrate member has a maximum radius, and at least 50% of the multi-petaled outer perimeter of the second double-sided adhesive substrate member extends to the maximum radius of the second double-sided adhesive substrate member.

5. The multi-petaled mounting member of claim 1, wherein the shape of the multi-petaled outer perimeter of the second double-sided adhesive substrate member corresponds to 3 to 6 petals.

6. The multi-petaled mounting member of claim 1, wherein the surrounding rim of the flexible plastic member is substantially annular.

7. The multi-petaled mounting member of claim 1, wherein the flexible plastic member further comprises mounting loops that are diametrically opposed and that extend radially outwardly from the surrounding rim to no further than the multi-petaled outer perimeter of the second double-sided adhesive substrate member and the multi-petaled outer perimeter of the adhesive skin barrier member.

8. The multi-petaled mounting member of claim 1, wherein the adhesive skin barrier member comprises an elastomer hydrocolloid mixture.

9. The multi-petaled mounting member of claim 1, wherein the first double-sided adhesive substrate member comprises a foam layer.

10. The multi-petaled mounting member of claim 1, wherein the second double-sided adhesive substrate member comprises a foam layer.

11. The multi-petaled mounting member of claim 1, further comprising a removable protective film, wherein the removable protective film covers the first face of the adhesive skin barrier member.

12. The multi-petaled mounting member of claim 1, wherein each of the flexible plastic member, the first double-sided adhesive substrate member, the second double-sided adhesive substrate member, and the adhesive skin barrier member have a stoma inlet portal, centrally positioned and extending therethrough.

13. An ostomy appliance comprising:
(a) the multi-petaled mounting member of claim 1, and
(b) an ostomy pouch,
wherein (i) the ostomy pouch comprises a proximal sheet of plastic film and a distal sheet of plastic film, the proximal sheet and the distal sheet being sealed at their respective peripheries to form the ostomy pouch, (ii) the proximal sheet comprises a stoma inlet portal having an inner perimeter and a zone surrounding the inner perimeter, (iii) the surrounding rim of the flexible plastic member further comprises an inner perimeter, (iv) the inner perimeter of the surrounding rim of the flexible plastic member substantially corresponds in size and shape to the inner perimeter of the stoma inlet portal of the proximal sheet, and (v) the surrounding rim of the flexible plastic member is sealed to the zone surrounding the inner perimeter of the proximal sheet.

14. A method of adhering an ostomy appliance to an ostomate at a peristomal skin surface of the ostomate, the ostomy appliance comprising:
(a) the multi-petaled mounting member of claim 11; and
(b) an ostomy pouch,
wherein each of the flexible plastic member, the first double-sided adhesive substrate member, the second double-sided adhesive substrate member, and the adhesive skin barrier member have a stoma inlet portal, centrally positioned and extending therethrough, and
further wherein (i) the ostomy pouch comprises a proximal sheet of plastic film and a distal sheet of plastic film, the proximal sheet and the distal sheet being sealed at their respective peripheries to form the ostomy pouch, (ii) the proximal sheet comprises a stoma inlet portal having an inner perimeter and a zone surrounding the inner perimeter, (iii) the surrounding rim of the flexible plastic member further comprises an inner perimeter, (iv) the inner perimeter of the surrounding rim of the flexible plastic member substantially corresponds in size and shape to the inner perimeter of the stoma inlet portal of the proximal sheet, and (v) the surrounding rim of the flexible plastic member is sealed to the zone surrounding the inner perimeter of the proximal sheet,
the method comprising the steps of:
(1) removing the removable protective film from the first face of the adhesive skin barrier member; and
(2) placing the first face of the adhesive skin barrier member at the peristomal region of the ostomate, such that the stoma inlet portal of the proximal sheet of the ostomy pouch and the stoma inlet portals of the flexible plastic member, the first double-sided adhesive substrate member, the second double-sided adhesive substrate member, and the adhesive skin barrier member are aligned with a stoma of the ostomate,
thereby adhering the ostomy appliance to the ostomate at the peristomal skin surface of the ostomate.

15. The method of claim 14, wherein the ostomy appliance adheres to the ostomate at the peristomal skin surface of the ostomate with a smooth fit.

16. The method of claim 14, wherein the ostomy appliance adheres to the ostomate at the peristomal skin surface of the ostomate without application of adhesive tape to the ostomy appliance or to the ostomate.

17. A method of adhering an ostomy appliance to an ostomate at a peristomal skin surface of the ostomate, the ostomy appliance comprising:
(a) the multi-petaled mounting member of claim 11; and
(b) an ostomy pouch,
wherein (i) the ostomy pouch comprises a proximal sheet of plastic film and a distal sheet of plastic film, the proximal sheet and the distal sheet being sealed at their respective peripheries to form the ostomy pouch, (ii) the proximal sheet comprises a stoma inlet portal having an inner perimeter and a zone surrounding the inner perimeter, (iii) the surrounding rim of the flexible plastic member further comprises an inner perimeter, (iv) the inner perimeter of the surrounding rim of the flexible plastic member substantially corresponds in size and shape to the inner perimeter of the stoma inlet portal of the proximal sheet, and (v) the surrounding rim of the flexible plastic member is sealed to the zone surrounding the inner perimeter of the proximal sheet,
the method comprising the steps of:
(1) removing the removable protective film from the first face of the adhesive skin barrier member;
(2) cutting a stoma inlet portal through each of: the flexible plastic member; the first double-sided adhesive substrate member; the second double-sided adhesive substrate member; and the adhesive skin barrier, to provide each with the stoma inlet portal, centrally positioned and extending therethrough,
(3) placing the first face of the adhesive skin barrier member at the peristomal region of the ostomate, such that the stoma inlet portal of the proximal sheet of the ostomy pouch and the stoma inlet portals of the flexible plastic member, the first double-sided adhesive substrate member, the second double-sided adhesive substrate member, and the adhesive skin barrier member are aligned with a stoma of the ostomate,
thereby adhering the ostomy appliance to the ostomate at the peristomal skin surface of the ostomate.

18. The method of claim 17, wherein the ostomy appliance adheres to the ostomate at the peristomal skin surface of the ostomate with a smooth fit.

19. The method of claim 17, wherein the ostomy appliance adheres to the ostomate at the peristomal skin surface of the ostomate without application of adhesive tape to the ostomy appliance or to the ostomate.

20. The mounting assembly of claim 1, wherein the width of each of the 2 to 8 petals is a width measured as an arcuate length with respect to a center of the adhesive skin barrier member.

* * * * *